United States Patent
Pudil et al.

(10) Patent No.: US 10,071,323 B2
(45) Date of Patent: Sep. 11, 2018

(54) MODULE FOR IN-LINE RECHARGING OF SORBENT MATERIALS WITH OPTIONAL BYPASS

(71) Applicant: MEDTRONIC, INC, Minneapolis, MN (US)

(72) Inventors: Bryant J. Pudil, Plymouth, MN (US); Martin T. Gerber, Maple Grove, MN (US); David B. Lura, Maple Grove, MN (US); Thomas E. Meyer, Stillwater, MN (US)

(73) Assignee: MEDTRONIC, INC, Minneapolis, MN (US)

( * ) Notice: Subject to any disclaimer, the term of this patent is extended or adjusted under 35 U.S.C. 154(b) by 677 days.

(21) Appl. No.: 14/626,281

(22) Filed: Feb. 19, 2015

(65) Prior Publication Data

US 2015/0157960 A1    Jun. 11, 2015

Related U.S. Application Data

(63) Continuation of application No. 14/259,665, filed on Apr. 30, 2014, now Pat. No. 9,943,780.
(Continued)

(51) Int. Cl.
*B01D 15/20* (2006.01)
*A61M 1/36* (2006.01)
(Continued)

(52) U.S. Cl.
CPC ......... *B01D 15/203* (2013.01); *A61M 1/1621* (2014.02); *A61M 1/1696* (2013.01);
(Continued)

(58) Field of Classification Search
CPC ............... B01D 15/203; B01J 2220/62; B01J 49/00–49/90; A61M 1/1696
(Continued)

(56) References Cited

U.S. PATENT DOCUMENTS

| | | | |
|---|---|---|---|
| 1,617,288 A * | 2/1927 | Kenney | C02F 1/42 210/190 |
| 3,608,729 A | 9/1971 | Haselden | |

(Continued)

FOREIGN PATENT DOCUMENTS

| | | |
|---|---|---|
| CN | 1487853 A | 4/2004 |
| CN | 104936633 | 9/2015 |

(Continued)

OTHER PUBLICATIONS

PCT Application, PCT/US20013/020404, filed Jan. 4, 2013.
(Continued)

*Primary Examiner* — Terry K Cecil
(74) *Attorney, Agent, or Firm* — Kenneth Collier; Roger Hahn

(57) ABSTRACT

This disclosure generally relates to at least one reusable module of a sorbent cartridge in a sorbent dialysis system and a method of using the same. One of the drawbacks of a conventional sorbent dialysis system is the high cost. In one aspect of the invention, the sorbent cartridge contains at least one module for optionally recharging sorbent materials in-line with an optional bypass and conduits for the sorbent cartridge. The sorbent cartridge can have two or more modules that are connected to one another through connectors. The modules can be reusable and the sorbent materials contained in the modules can be recharged.

22 Claims, 21 Drawing Sheets

Related U.S. Application Data

(60) Provisional application No. 61/945,064, filed on Feb. 26, 2014, provisional application No. 61/941,672, filed on Feb. 19, 2014, provisional application No. 61/909,372, filed on Nov. 26, 2013.

(51) Int. Cl.
  *B01J 20/34* (2006.01)
  *B01D 15/10* (2006.01)
  *A61M 1/16* (2006.01)

(52) U.S. Cl.
  CPC .............. *A61M 1/367* (2013.01); *B01D 15/10* (2013.01); *B01J 20/3416* (2013.01); *B01J 20/3425* (2013.01); *B01J 20/3433* (2013.01); *B01J 20/3475* (2013.01); *A61M 2202/0468* (2013.01); *A61M 2205/128* (2013.01); *A61M 2205/3334* (2013.01); *B01J 2220/62* (2013.01)

(58) Field of Classification Search
  USPC .......................................................... 210/677
  See application file for complete search history.

(56) References Cited

U.S. PATENT DOCUMENTS

| | | | |
|---|---|---|---|
| 3,617,558 | A * | 11/1971 | Jones ............... B01J 39/05 210/279 |
| 3,669,880 | A * | 6/1972 | Marantz ............. A61M 1/1696 210/632 |
| 3,776,819 | A | 12/1973 | Williams |
| 3,850,835 | A | 11/1974 | Marantz |
| 3,884,808 | A | 5/1975 | Scott |
| 3,902,490 | A | 9/1975 | Jacobsen et al. |
| 3,989,622 | A | 11/1976 | Marantz |
| 4,094,775 | A | 6/1978 | Mueller |
| 4,206,054 | A | 6/1980 | Moore |
| 4,209,392 | A | 6/1980 | Wallace |
| 4,376,707 | A | 3/1983 | Lehmann |
| 4,460,555 | A | 7/1984 | Thompson |
| 4,581,141 | A | 4/1986 | Ash |
| 4,650,587 | A | 3/1987 | Polak |
| 4,684,460 | A | 8/1987 | Issautier |
| 4,687,582 | A | 8/1987 | Dixon |
| 5,230,702 | A | 7/1993 | Lindsay et al. |
| 5,284,470 | A | 2/1994 | Beltz |
| 5,302,288 | A | 4/1994 | Meidl |
| 5,308,315 | A | 5/1994 | Khuri |
| 5,507,723 | A | 4/1996 | Keshaviah |
| 5,662,806 | A | 9/1997 | Keshaviah et al. |
| 5,770,086 | A | 6/1998 | Indriksons |
| 5,849,179 | A | 12/1998 | Emerson et al. |
| 5,858,186 | A | 1/1999 | Glass |
| 5,944,684 | A | 8/1999 | Roberts |
| 6,036,858 | A | 3/2000 | Carlsson |
| 6,114,176 | A | 9/2000 | Edgson et al. |
| 6,126,831 | A | 10/2000 | Goldau et al. |
| 6,521,184 | B1 | 2/2003 | Edgson et al. |
| 6,572,769 | B2 | 6/2003 | Rajan |
| 6,579,460 | B1 | 6/2003 | Willis |
| 6,627,164 | B1 | 9/2003 | Wong |
| 6,666,840 | B1 | 12/2003 | Falkvall et al. |
| 6,719,745 | B1 | 4/2004 | Taylor |
| 6,814,724 | B2 | 11/2004 | Taylor |
| 6,818,196 | B2 | 11/2004 | Wong |
| 6,861,266 | B1 | 3/2005 | Sternby |
| 6,878,283 | B2 | 4/2005 | Thompson |
| 6,878,285 | B2 * | 4/2005 | Hughes ............... B01J 39/04 210/663 |
| 6,960,179 | B2 | 11/2005 | Gura |
| 7,033,498 | B2 | 4/2006 | Wong |
| 7,101,519 | B2 | 9/2006 | Wong |
| 7,208,092 | B2 | 4/2007 | Micheli |
| 7,241,272 | B2 | 7/2007 | Karoor |
| 7,276,042 | B2 | 10/2007 | Polaschegg |
| 7,326,576 | B2 | 2/2008 | Womble et al. |
| 7,435,342 | B2 | 10/2008 | Tsukamoto |
| 7,488,447 | B2 | 2/2009 | Sternby |
| 7,537,688 | B2 | 5/2009 | Tarumi et al. |
| 7,544,300 | B2 | 6/2009 | Brugger et al. |
| 7,544,737 | B2 | 6/2009 | Poss et al. |
| 7,563,240 | B2 | 7/2009 | Gross et al. |
| 7,566,432 | B2 | 7/2009 | Wong |
| 7,597,806 | B2 | 10/2009 | Uchi |
| 7,794,419 | B2 | 7/2010 | Paolini et al. |
| 7,776,210 | B2 | 8/2010 | Rosenbaum |
| 7,850,635 | B2 | 12/2010 | Polaschegg |
| 7,922,686 | B2 | 4/2011 | Childers et al. |
| 7,922,911 | B2 | 4/2011 | Micheli |
| 7,947,179 | B2 | 5/2011 | Rosenbaum |
| 7,955,290 | B2 | 6/2011 | Karoor et al. |
| 7,988,854 | B2 | 8/2011 | Tsukamoto |
| 8,002,726 | B2 | 8/2011 | Karoor |
| 8,012,118 | B2 | 9/2011 | Curtin |
| 8,029,454 | B2 | 11/2011 | Kelly et al. |
| 8,066,658 | B2 | 11/2011 | Karoor et al. |
| 8,080,161 | B2 | 12/2011 | Ding et al. |
| 8,087,303 | B2 | 1/2012 | Beavis |
| 8,096,969 | B2 | 1/2012 | Roberts |
| 8,180,574 | B2 | 5/2012 | Lo et al. |
| 8,187,250 | B2 | 5/2012 | Roberts |
| 8,197,439 | B2 | 6/2012 | Wang et al. |
| 8,303,532 | B2 | 11/2012 | Hamada et al. |
| 8,404,491 | B2 | 3/2013 | Ding et al. |
| 8,409,444 | B2 | 4/2013 | Wong |
| 8,480,607 | B2 | 7/2013 | Davies |
| 8,647,506 | B2 | 2/2014 | Wong |
| 8,733,559 | B2 | 5/2014 | Wong |
| 8,764,981 | B2 | 7/2014 | Ding |
| 8,777,892 | B2 | 7/2014 | Sandford |
| 9,144,640 | B2 | 9/2015 | Pudil |
| 9,254,355 | B2 * | 2/2016 | Sandford ............... A61M 1/284 |
| 2001/0007931 | A1 | 7/2001 | Blatter |
| 2002/0112609 | A1 | 8/2002 | Wong |
| 2002/0117436 | A1 | 8/2002 | Rajan |
| 2003/0080059 | A1 | 5/2003 | Peterson et al. |
| 2003/0097086 | A1 | 5/2003 | Gura |
| 2003/0105435 | A1 | 6/2003 | Taylor |
| 2003/0113931 | A1 | 6/2003 | Pan |
| 2003/0114787 | A1 | 6/2003 | Gura |
| 2004/0019312 | A1 | 1/2004 | Childers et al. |
| 2004/0099593 | A1 | 5/2004 | DePaolis |
| 2004/0147900 | A1 | 7/2004 | Polaschegg |
| 2004/0168963 | A1 | 9/2004 | King |
| 2004/0257409 | A1 | 12/2004 | Cheok |
| 2005/0006296 | A1 | 1/2005 | Sullivan |
| 2005/0113796 | A1 | 5/2005 | Taylor |
| 2005/0150832 | A1 | 7/2005 | Tsukamoto |
| 2005/0274658 | A1 | 12/2005 | Rosenbaum |
| 2006/0241543 | A1 | 10/2006 | Gura |
| 2007/0007208 | A1 | 1/2007 | Brugger et al. |
| 2007/0179431 | A1 | 8/2007 | Roberts |
| 2007/0213665 | A1 | 9/2007 | Curtin |
| 2008/0006570 | A1 | 1/2008 | Gura |
| 2008/0051696 | A1 | 2/2008 | Curtin |
| 2008/0053905 | A9 | 3/2008 | Brugger et al. |
| 2008/0217245 | A1 | 9/2008 | Rambod |
| 2009/0020471 | A1 | 1/2009 | Tsukamoto |
| 2009/0078636 | A1 | 3/2009 | Uchi |
| 2009/0101552 | A1 | 4/2009 | Fulkerson |
| 2009/0120864 | A1 | 5/2009 | Fulkerson |
| 2009/0157877 | A1 | 6/2009 | Baek |
| 2009/0216045 | A1 | 8/2009 | Singh |
| 2009/0266358 | A1 | 10/2009 | Sacristan Rock |
| 2010/0004588 | A1 | 1/2010 | Yeh |
| 2010/0007838 | A1 | 1/2010 | Fujimoto |
| 2010/0078381 | A1 | 4/2010 | Merchant |
| 2010/0078387 | A1 | 4/2010 | Wong |
| 2010/0084330 | A1 | 4/2010 | Wong |
| 2010/0100027 | A1 | 4/2010 | Schilthuizen |
| 2010/0101195 | A1 | 4/2010 | Clements |
| 2010/0102190 | A1 | 4/2010 | Zhu et al. |
| 2010/0114012 | A1 | 5/2010 | Sandford |
| 2010/0217181 | A1 | 8/2010 | Roberts |

(56) References Cited

U.S. PATENT DOCUMENTS

| | | |
|---|---|---|
| 2010/0224492 A1 | 9/2010 | Ding et al. |
| 2010/0312172 A1 | 12/2010 | Hoffman |
| 2010/0314314 A1 | 12/2010 | Ding |
| 2011/0009798 A1 | 1/2011 | Kelly |
| 2011/0017665 A1 | 1/2011 | Updyke |
| 2011/0048949 A1 | 3/2011 | Ding et al. |
| 2011/0163034 A1 | 7/2011 | Castellarnau |
| 2011/0171713 A1 | 7/2011 | Bluchel |
| 2011/0184340 A1 | 7/2011 | Tan |
| 2011/0272352 A1 | 11/2011 | Braig |
| 2011/0297593 A1 | 12/2011 | Kelly |
| 2012/0018377 A1 | 1/2012 | Tsukamoto |
| 2012/0248017 A1 | 10/2012 | Beiriger |
| 2013/0018095 A1 | 1/2013 | Vath |
| 2013/0019179 A1 | 1/2013 | Zhao |
| 2013/0027214 A1 | 1/2013 | Eng |
| 2013/0028809 A1 | 1/2013 | Barton |
| 2013/0199998 A1 | 8/2013 | Kelly |
| 2013/0213890 A1 | 8/2013 | Kelly |
| 2013/0213891 A1 | 8/2013 | Karoor |
| 2014/0001112 A1 | 1/2014 | Karoor |
| 2014/0138294 A1 | 5/2014 | Fulkerson |
| 2014/0190885 A1 | 7/2014 | Meyer |
| 2014/0217028 A1 | 8/2014 | Pudil |
| 2014/0251908 A1 | 9/2014 | Ding |
| 2014/0326671 A1 | 11/2014 | Kelly |
| 2015/0057602 A1 | 2/2015 | Mason |
| 2015/0108609 A1 | 4/2015 | Kushida |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0258266 A1 | 9/2015 | Merchant |
| 2015/0306292 A1 | 10/2015 | Pudil |
| 2015/0367051 A1 | 12/2015 | Gerber |
| 2015/0367052 A1 | 12/2015 | Gerber |
| 2015/0367056 A1 | 12/2015 | Gerber |
| 2015/0367057 A1 | 12/2015 | Gerber |
| 2015/0367058 A1 | 12/2015 | Gerber |
| 2015/0367059 A1 | 12/2015 | Gerber |
| 2015/0367060 A1 | 12/2015 | Gerber |

FOREIGN PATENT DOCUMENTS

| | | |
|---|---|---|
| CN | 105658326 A | 6/2016 |
| EP | 711182 B1 | 6/2003 |
| EP | 1592494 B1 | 6/2009 |
| EP | 2575827 A2 | 12/2010 |
| EP | 2576453 A2 | 12/2011 |
| EP | 2446908 | 5/2012 |
| EP | 1545652 B1 | 1/2013 |
| EP | 1345856 B1 | 3/2013 |
| EP | 2344220 B1 | 4/2013 |
| JP | S51-55193 | 5/1976 |
| JP | S51-131393 | 11/1976 |
| JP | S61164562 | 7/1986 |
| JP | 2981573 | 11/1999 |
| JP | 2005511250 | 4/2005 |
| JP | 2013502987 | 1/2013 |
| WO | 9532010 A1 | 11/1995 |
| WO | 0185295 A2 | 11/2001 |
| WO | 2002043859 | 6/2002 |
| WO | 2003043677 A2 | 5/2003 |
| WO | 2003051422 A2 | 6/2003 |
| WO | 2004064616 A2 | 8/2004 |
| WO | 2004062710 A3 | 10/2004 |
| WO | 2005123230 A2 | 12/2005 |
| WO | 2007089855 A2 | 8/2007 |
| WO | 2008075951 A1 | 6/2008 |
| WO | 2009157877 A1 | 12/2009 |
| WO | 2009157878 A1 | 12/2009 |
| WO | 2010028860 A1 | 2/2010 |
| WO | 2010102190 A4 | 11/2010 |
| WO | 2010141949 | 12/2010 |
| WO | WO 2011/017215 | 2/2011 |
| WO | 2013/019179 | 2/2013 |
| WO | 2013019179 | 2/2013 |
| WO | 2013019179 A1 | 2/2013 |
| WO | 2013025957 | 2/2013 |
| WO | 2013027214 | 2/2013 |
| WO | 2013028809 | 2/2013 |
| WO | 2013028809 A3 | 2/2013 |
| WO | 2013019994 A3 | 4/2013 |
| WO | 2012060700 | 5/2013 |
| WO | 2013025844 A3 | 5/2013 |
| WO | 2013101888 | 7/2013 |
| WO | 2013103607 A1 | 7/2013 |
| WO | 2013103906 | 7/2013 |
| WO | 2015142624 | 9/2015 |
| WO | 2015199764 | 12/2015 |

OTHER PUBLICATIONS

U.S. Appl. No. 13/836,973, filed Mar. 15, 2013.
U.S. Appl. No. 14/259,655, filed Apr. 23, 2014.
U.S. Appl. No. 14/259,589, filed Apr. 23, 2014.
PCT/US2014/065950 International Search Report and Written Opinion dated Feb. 24, 2015.
PCT/US2015/032492 International Search Report dated Nov. 19, 2015.
PCT/US2015/016270 International Search Report and Written Opinion dated Jun. 5, 2015.
PCT/US2015/016273 International Search Report and Written Opinion dated Jun. 9, 2015.
PCT/US2015/032492 Written Opinion dated Nov. 19, 2015.
PCT/US2015/020046 International Search Report and Written Opinion dated Jun. 29, 2015.
International Search Report from PCT/US2012/051946.
U.S. Appl. No. 61/526,209.
U.S. Appl. No. 13/757,693, filed Jan. 4, 2013.
U.S. Appl. No. 13/836,079, filed Mar. 15, 2013.
U.S. Appl. No. 14/240,129, filed Aug. 22, 2013.
U.S. Appl. No. 13/835,735, filed Mar. 15, 2013.
PCT/US2015/020044 International Search Report Written Opinion dated Jun. 30, 2015.
PCT/US15/18587 International Preliminary Report on Patentability dated Jun. 6, 2016.
Office Action for Chinese Application No. 2015/80009562.5 dated Jul. 3, 2017.
International Preliminary Report on Patentability for Application No. PCT/US2015/032492 dated Jun. 30, 2017.
International Preliminary Report on Patentability for Application No. PCT/US2015/016273 dated Feb. 19, 2016.
European Search Report for App. No. 15751391.2 dated Aug. 4, 2017.
European Search Report and supplementary Search Report for App. No. 14865374.4 dated Jun. 12, 2017.
[NPL10] Wheaton, et al., Dowex Ion Exchange Resins—Fundamentals of Ion Exchange; Jun. 2000, pp. 1-9. http://www.dow.com/scripts/litorder.asp?filepath=liquidseps/pdfs/noreg/177-01837.pdf.
European Search Report for App. No. 15812081.6, dated Mar. 8, 2018
European Search Report for EP App. No. 15811326.6, dated Feb. 14, 2018.
European Search Report for EP App. No. 15812413.1, dated Feb. 2, 2018.

* cited by examiner

MODULE FOR IN-LINE RECHARGING OF SORBENT MATERIALS WITH OPTIONAL BYPASS The present application is a continuation of U.S. utility application Ser. No. 14/259,665, filed Apr. 23, 2014, which claims priority to provisional application No. 61/945,064, filed Feb. 26, 2014, provisional application No. 61/941,672, filed Feb. 19, 2014, and provisional application No. 61/909,372, filed Nov. 26, 2013; and each of which is hereby incorporated by reference.

FIELD OF THE INVENTION

The invention relates to modules for optional in-line recharging of sorbent materials in a sorbent cartridge. The modules can be detachable, and the sorbent materials can include zirconium phosphate.

BACKGROUND

Dialysis involves the movement of blood through a dialyzer that has a semi-permeable membrane. Simultaneously, dialysate is circulated through the dialyzer on an opposite side of the semi-permeable membrane. Toxins present in the blood stream of the patient pass from the blood through the membrane into the dialysate. After passing through the dialyzer, the spent dialysate is discarded. Disposal of spent dialysate requires a large amount of source water for preparing the replacement dialysate necessary for use during continuous dialysis. However, in sorbent dialysis systems, the spent dialysate is re-circulated through a sorbent cartridge rather than being discarded. The sorbent cartridge contains layers of sorbent material which selectively remove specific toxins, or break down toxins, in the dialysate.

The advantage of sorbent dialysis is that a much lower amount of water is required. In four hours of traditional dialysis, up to 120 L of water may be required to generate the dialysate. By contrast, using sorbent dialysis, as little as 6 or 7 L of water may be necessary. Thus, the need for drains and a continuous source of purified water are eliminated, rendering the system portable.

One of the drawbacks of sorbent dialysis systems is the high cost. The materials used in the sorbent cartridges can be expensive. Disposing of the cartridges after each use generates waste and drives up costs. Other known dialysate fluid circulation systems and apparatuses have separate housings where a first housing has a material capable of releasing sodium into dialysate fluid flowing through the first housing, and a second housing has a material capable of binding sodium ions from dialysate fluid flowing through the second housing. However, such systems cannot be formed into a single housing design, oftentimes require many liters of water, and may not be portable. The systems also do not provide for recharging some or all of the components of a sorbent cartridge that would allow reuse of specific components and enable lower long-term costs for operating such systems.

Hence, there is a need for a sorbent cartridge having a separation of materials within the sorbent cartridge into modules to allow for isolation of those materials. There is a need for a sorbent cartridge providing for isolation of one or more sorbent materials to allow for cheaper or non-reusable materials to be discarded, while more expensive and reusable materials are recharged. There is further need for a unitary sorbent cartridge having multiple discreet modules that can be easily connected and/or detached from the unitary sorbent cartridge thereby facilitating the recharging and/or recycling of the sorbent materials and the sorbent cartridge while retaining a single unitary design. There is also a need for a modular sorbent cartridge having the features of reduced size and weight necessary for a portable dialysis machine. There is a need for a modular sorbent cartridge wherein the sorbent materials can be arranged within the modules of the cartridge to allow for isolation of particular materials or groups of materials. There is further a need for any one of the modules in the cartridge to be reusable or optionally detachable from the cartridge to allow any one of disposal, recycling or recharging of sorbent material within the module. There is a need for a sorbent cartridge having specific materials that can be recharged and allowing for disposal of less expensive materials.

There is a need for the sorbent materials to be recharged without removing the modules from the sorbent cartridge during operation, making the system easier to use. There is a need for a recharging means directly attached to the sorbent modules, to allow the modules to be recharged simply by directing fluid flow from the rechargers to the module. There is further a need for one or more of the modules to be removable to allow for the recycling and/or disposal of these modules, while allowing for the recharging of other modules.

SUMMARY OF THE INVENTION

The present invention relates to a sorbent cartridge comprising at least one reusable module. In any embodiment, the sorbent cartridge can have one or more reusable modules having one or more connectors fluidly connectable to any part of a fluid flow path selected from any one of a wash line, a fluid line, or a bypass line. In any embodiment, the wash line can optionally be fluidly connectable to a recharger, and the bypass line can optionally be fluidly connectable to another module. Moreover, the fluid line can be optionally fluidly connectable to any portion of a dialysis circuit.

In any embodiment, at least one valve can be positioned before and/or after the modules on the connectors to selectively direct flow through at least one module, wash line, recharger, and/or bypass line. The flow can be comprised of either gas or liquid.

In any embodiment, the sorbent cartridge can have one or more modules that make up the sorbent cartridge. The one or more detachable cartridges can be reusable or non-reusable.

In any embodiment, any one of four-way, three-way, two-way valves, or combinations thereof, can be positioned before and/or after the modules on the connectors to selectively direct flow through the modules, wash line, recharger, or bypass line.

In any embodiment, the sorbent cartridge can be configured so that the reusable module is in an off-line state by being fluidly connectable to a recharger. In yet another embodiment, the reusable module can be configured to be in an in-line state by being fluidly connectable to any one of the fluid line or the bypass line.

In any embodiment, a first module, which can be a reusable module, and the second module can be connected in series. A first bypass line can connect a first valve, positioned on a connector before the first module, to a second valve. A second bypass line can connect the second valve to a third valve positioned on a connector between the first and second module. A third bypass line can connect the second valve and a fourth valve positioned on a connector after the second module.

In any embodiment, the first module, which can be a reusable module, and the second module can be connected in series such that a first valve can be positioned on a connector before the first module, and can connect a bypass line to a second valve positioned on a connector between the first and second modules. The bypass line can further connect to a third valve positioned on a connector after the second module.

In any embodiment, the first module, which can be a reusable module, and the second module can be connected in series, and a first bypass line can connect a first valve, positioned on a connector before the first module, to a second valve positioned on a connector between the first and second modules. A second bypass line can connect a third valve, positioned on the connector between the first and second module, to a fourth valve positioned on a connector after the second module.

In any embodiment, a first module, which can be a reusable module, and the second module can be connected in series, and a first bypass line can connect a first valve positioned on a connector before the first module to a second valve positioned on a connector between the first module and the second module. A second bypass line can connect a third valve positioned on the connector between the first and second modules to a fourth valve positioned on a connector after the second module. A first wash line can connect the first valve to a first recharger connector or node, a second wash line can connect the second valve to the first recharger connector or node, a third wash line can connect the third valve to a second recharger connector or node, and a fourth wash line can connect the fourth valve to the second recharger connector or node.

In any embodiment, a first module, which can be a reusable module, and the second module can be connected in series. A first valve positioned on a connector before the first module can connect a first wash line to a first recharger connector. A second wash line can connect a second valve, positioned on a connector between the first and second modules, to the first recharger connector; a third wash line can connect a third valve, positioned on the connector between the first and second modules, to a second recharger connector; and a fourth wash line can connect a fourth valve, positioned on a connector after the second module, to the second recharger connector. A fifth valve, positioned on the connector before the first module, can connect a bypass line to a sixth valve positioned on the connector between the first module and the second module, and can further connect to a seventh valve positioned on the connector after the second module.

In any embodiment, the sorbent cartridge can comprise at least one reusable removable module with one or more connectors.

In any embodiment, the sorbent cartridge can comprise at least one non-reusable module.

In any embodiment, the reusable module can contain sorbent material.

In any embodiment, the reusable module can contain multiple sorbent materials.

In any embodiment the non-reusable module can contain sorbent material.

In any embodiment, the non-reusable sorbent module can contain multiple sorbent materials.

In any embodiment, the connectors connecting the modules may be selected from a group comprising quick-connect, twist-lock, push-on and threaded fittings.

In any embodiment, the connectors may comprise a length of tubing and a valve or a valve assembly.

In any embodiment, the at least one reusable module is detachable from the sorbent cartridge.

In any embodiment, the reusable module contains sorbent materials that may be selected from a group comprising zirconium phosphate, hydrous zirconium oxide, activated carbon, alumina, urease and ion exchange resin. In any embodiment, the ion-exchange resin can be selected to only remove sodium, potassium, calcium and magnesium ions. The ion exchange resin can also be a chelating ion-exchange resin. The respective layers can be formed into any combination of layers without restriction.

In any embodiment, the non-reusable module contains sorbent materials that may be selected from a group comprising zirconium phosphate, hydrous zirconium oxide, activated carbon, alumina, urease and ion exchange resin. In any embodiment, the ion-exchange resin can be selected to only remove sodium, potassium, calcium and magnesium ions. The ion-exchange resin can also be a chelating ion-exchange resin. The respective layers can be formed into any combination of layers without restriction.

In any embodiment, the reusable module may be recyclable and/or rechargeable.

In any embodiment, at least one module may have a barcode or other identification system.

In any embodiment, the connectors may include an access point for a sensor.

The invention also relates to a fluid circuit. In one embodiment, the fluid circuit can have at least two modules connected by one or more connectors in series. An operational line can direct flow along the connectors and through the modules. A wash line can fluidly connect one or more connectors to a recharger. A bypass line can bypass the modules and the operational line.

In any embodiment, the bypass line of the fluid circuit can be in fluid communication with at least one sorbent material.

The invention also relates to a method of recharging a sorbent. In one embodiment, the method can include connecting at least a first module, which can be a reusable module, and second module in series with one or more connectors. At least one connector can be fluidly connected to at least one wash line, and the at least one wash line can be fluidly connected to a recharger. At least one connector can be fluidly connected to a bypass line. The bypass line can divert flow from the connector to bypass at least one module. The method can include connecting a valve assembly having one or more valves to the connectors at junctions between the modules, wash lines and/or bypass lines. The method can include selectively opening and closing the valves to direct flow through the connectors, modules, wash lines and/or bypass lines.

In any embodiment, the method can include a valve assembly having one or more valves positioned on a connector before a first module, which can be a reusable module. The valve assembly can connect the connector, a wash line, and a bypass line. The valve assembly can be open to the wash line and closed to the connector and the bypass line such that flow is directed to a recharger. The flow can be redirected to the recharger through the washline, and into the reusable module.

In any embodiment, the method can include a valve positioned on a connector before the first module, which can be a reusable module. The valve can connect the connector, a wash line, and a bypass line. The valve can be open to the wash line and connector and closed to the bypass line such that flow circulates between the first module and the recharger. A second valve assembly having one or more values can be positioned on a connector between the first module and the second module and can be closed such that flow cannot continue from the first module to the second module. The second value assembly can connect the connector, a second wash line and a bypass line. The second valve assembly can be open to the second wash line and reusable module, and closed to the second module and bypass line, such that flow circulates between the recharger and the reusable module.

In any embodiment, the method can include an assembly having one or more valve positioned on a connector before the first module, which can be a reusable module. The valve can connect the connector, a wash line, and a bypass line. The valve assembly can be open to the bypass line and closed to the wash line and connector, such that flow is directed through the bypass line to bypass the first module. The valve assembly can be open to the wash line and connector, and closed to the bypass line such that flow circulates between the reusable module and the recharger, but a second valve assembly positioned on a connector between the reusable module and a second module is closed such that flow cannot continue from the reusable module to the second module.

In any embodiment, the method includes a valve assembly having one or more valves positioned on a connector before the first module, which can be a reusable module. The valve assembly can connect the connector, a wash line, and a bypass line. The valve assembly can be open to the connector and closed to the bypass and wash lines, such that flow is directed through the connector and through the first module. The valve assembly can be open to the bypass line, and closed to the wash line and the connector, such that flow is directed through the bypass line to bypass the reusable module.

In any embodiment, the method can include a pump attached to the recharger or wash line.

In any embodiment a gas, such as argon, air, filtered air, nitrogen, and helium can be used to blow out the module.

In any embodiment the wash lines can be subdivided into a top and a bottom wash line.

In any embodiment, the top line can be a fluid line and the bottom line can be a gas line.

In any embodiment, the top line can be a gas line and the bottom line can be a fluid line.

In any embodiment the top and bottom lines can both be fluid lines.

In any embodiment, the at least two modules can be part of a controlled compliant dialysis circuit.

In any embodiment, the valves can be operated under control of a programmable controller or computer system to regulate flow into, out of, and between modules.

In any embodiment, fluid flow through the valves may be sensed by a photocell or other flow sensing and/or measuring apparatus.

In any embodiment, a control pump can circulate fluid in the flow path.

In any embodiment, the sorbent materials may be mixed together.

In any embodiment, the one or more sorbent materials are selected from the group consisting of zirconium phosphate, hydrous zirconium oxide, activated carbon, alumina, urease and ion exchange resin.

In any embodiment, at least one of the reusable module and second module contain multiple sorbent materials.

In any embodiment, the reusable module and second module comprise a single sorbent cartridge.

In any embodiment, the reusable module may not be detached from the sorbent cartridge before recharging.

In any embodiment, the second module can be a reusable module.

In any embodiment, the method can comprise fluidly connecting at least a second connector positioned between the reusable module and the second module to at least a second wash line, where the second wash line is fluidly connected to a second recharger, fluidly connecting the second connector to a second bypass line, and the second bypass line diverts flow from the second connector to bypass at least one module, connecting a second valve assembly to the connectors at junctions between the modules, wash lines and/or bypass lines, and selectively opening and closing the second valve assembly to direct flow through the connectors, modules, wash lines and/or bypass lines.

In any embodiment, the one or more sorbent materials contained in the first reusable module are not identical to the one or more sorbent materials contained in the second module.

In any embodiment, the method can further comprise selectively opening and closing the first valve assembly and the second valve assembly such that flow is circulated between the first recharger and the first reusable module, and such that flow is circulated between the second recharger and the second module.

In any embodiment, the sorbent cartridge can have a first module, which can be a reusable module, and a second module connected in series. The first module can be fluidly connected to a first set of one or more valves positioned on a first set of one or more connectors before the first module, such that fluid may be directed into the first module. A bypass line can be fluidly connected to the first set of one or more valves such that fluid can bypass the first module. A first recharger can be fluidly connected to the first set of one or more valves such that fluid may be directed from the first recharger to the first module. The first module can be fluidly connected to a second set of one or more valves positioned on a second set of one or more connectors after the first module and before the second module, such that fluid may be directed from the first module into the second module. The bypass line can be fluidly connected to the second set of one or more valves such that fluid can bypass the second module. The first recharger can be connected to the second set of one or more valves such that fluid may be directed from the first module to the first recharger. A second recharger can be fluidly connected to the second set of one or more valves such that fluid may be directed from the second recharger to the second module. The second recharger can be fluidly connected to a third set of one or more connectors positioned after the second module such that fluid may be directed from the second module to the second recharger.

In any embodiment, the sorbent cartridge can have a first module, which can be a reusable module, and a second module connected in series. The first module can be fluidly connected to a first set of one or more valves positioned on a first set of one or more connectors before the first module, such that fluid may be directed into the first module. A bypass line can be fluidly connected to the first set of one or more valves such that fluid can bypass the first module. The first module and bypass line can be fluidly connected to a second set of one or more valves positioned on a second set of one or more connectors after the first module and before the second module, such that fluid may be directed from the first module into the second module. The bypass line can be fluidly connected to the second set of one or more valves such that fluid can bypass the second module.

In any embodiment, the sorbent cartridge can have a first module, a second module, and a third module connected in series. Any one of the modules can be reusable. The first module can be fluidly connected to a first set of one or more valves positioned on a first set of one or more connectors before the first module, such that fluid may be directed into the first module. A bypass line can be fluidly connected to the first set of one or more valves such that fluid can bypass the first module. A first recharger can be fluidly connected to the first set of one or more valves such that fluid may be directed from the first recharger to the first module. The first module can be fluidly connected to a second set of one or more valves positioned on a second set of one or more connectors after the first module and before the second module, such that fluid may be directed from the first module into the second module. The first recharger can be connected to the second set of one or more valves such that fluid may be directed from the first module to the first recharger. The bypass line can be fluidly connected to the second set of one or more valves such that fluid can bypass the second module. A second recharger can be fluidly connected to the second set of one or more valves such that fluid may be directed from the second recharger to the second module. The second module can be fluidly connected to a third set of one or more valves positioned on a third set of one or more connectors after the second module and before the third module, such that fluid may be directed from the second module into the third module. The second recharger can be fluidly connected to the third set of one or more valves such that fluid from the second module may be directed to the second recharger. The bypass line can be fluidly connected to the third set of one or more valves such that fluid can bypass the third module. A third recharger can be fluidly connected to the third set of one or more valves such that fluid may be directed from the third recharger to the third module. The third module can be fluidly connected to a fourth set of one or more connectors. The third recharger can be fluidly connected to the fourth set of one or more connectors such that fluid may be directed from the third module to the third recharger.

DETAILED DESCRIPTION OF THE INVENTION

Figure 1:
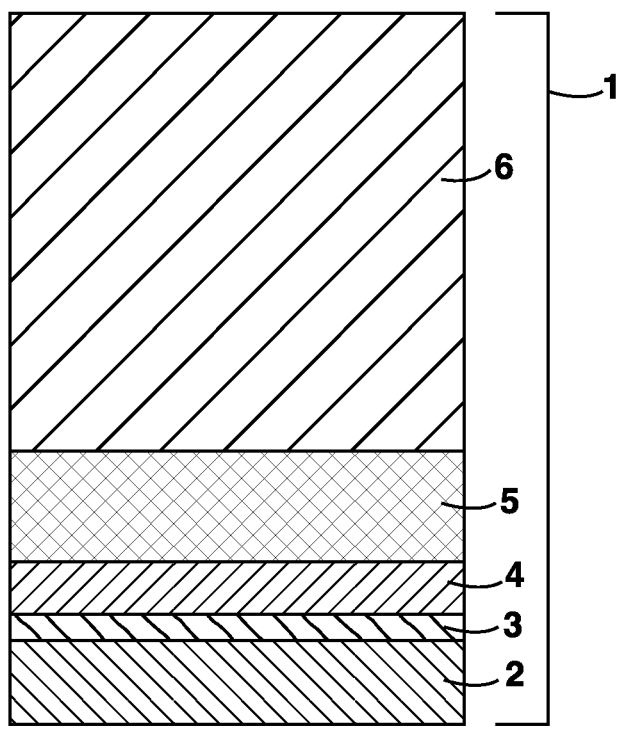
FIG. 1 shows a sorbent cartridge containing activated carbon, hydrous zirconium oxide, urease, alumina, and zirconium phosphate.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

"Blow out" refers to the process of passing a gas through a connection line or a module.

"Bypass line" refers to a line, connected to the main line, through which fluid or gas may alternatively flow.

The term "cartridge" refers to any container designed to contain a powder, liquid, or gas made for ready connection to a device or mechanism. The container can have one or more compartments. Instead of compartments, the container can also be comprised of a system of two or more modules connected together to form the cartridge wherein the two or more modules once formed can be connected to a device or mechanism.

The term "cation concentrate reservoir" refers to an object having or holding a substance that is comprised of at least one cation, for example calcium, magnesium, or potassium ions.

The term "cation infusate source" refers to a source from which cations can be obtained. Examples of cations include, but are not limited to, calcium, magnesium and potassium. The source can be a solution containing cations or a dry composition that is hydrated by the system. The cation infusate source is not limited to cations and may optionally include other substances to be infused into a dialysate or replacement fluid, non-limiting examples can be glucose, dextrose, acetic acid and citric acid.

The term "comprising" includes, but is not limited to, whatever follows the word "comprising." Thus, use of the term indicates that the listed elements are required or mandatory but that other elements are optional and may or may not be present.

A "connector" as used herein forms a fluid connection between two components wherein liquid or gas can flow from one component, through the connector, to another component. It will be understood that the connector provides for a fluid connection in its broadest sense and can include any type of tubing, fluid or gas passageway, or conduit between any one or more components of the invention.

The term "consisting of" includes and is limited to whatever follows the phrase "consisting of." Thus, the phrase indicates that the limited elements are required or mandatory and that no other elements may be present. The term "consisting essentially of" includes whatever follows the term "consisting essentially of" and additional elements, structures, acts or features that do not affect the basic operation of the apparatus, structure or method described. The term "container" as used herein in the context of a controlled compliant circuit is a receptacle that may be flexible or inflexible for holding any fluid or solid, such as for example a spent dialysate fluid, or a sodium chloride or sodium bicarbonate solution or solid, or the like.

The terms "controlled compliance" and "controlled compliant" describe the ability to actively control the transfer of fluid volume into or out of a compartment, flow path or circuit. In certain embodiments, the variable volume of fluid in a dialysate circuit or controlled compliant flow path expands and contracts via the control of one or more pumps in conjunction with one or more reservoirs. The volume of fluid in the system is generally constant (unless additional fluids are added to a reservoir from outside of the system) once the system is in operation if patient fluid volume(s), flow paths, and reservoirs are considered part of the total volume of the system (each individual volume may sometimes be referred to as a fluid compartment). The attached reservoirs allow the system to adjust the patient fluid volume by withdrawing fluid and storing the desired amount in an attached control reservoir and/or by providing purified and/or rebalanced fluids to the patient and optionally removing waste products. The terms "controlled compliance" and "controlled compliant" are not to be confused with the term "non-compliant volume," which simply refers to a vessel, conduit, container, flow path, conditioning flow path or cartridge that resists the introduction of a volume of fluid after air has been removed from a defined space such as a vessel, conduit, container, flow path, conditioning flow path or cartridge. In one embodiment, the controlled compliant system can move fluids bi-directionally. In certain cases, the bi-directional fluid movement can be across a semi-permeable membrane either inside or outside a dialyzer. The bi-directional fluid flow can also occur across, through, or between vessels, conduits, containers, flow paths, conditioning flow paths or cartridges of the invention in selected modes of operation. The term "moving fluid bi-directionally" as used in connection with a barrier, such as a semi-permeable membrane, refers to the ability to move fluid across the barrier in either direction. "Moving fluid bi-directionally" also can apply to the ability to move fluid in both directions in the flow path or between a flow path and reservoir in a controlled compliant system.

The terms "controlled compliant flow path," "controlled compliant dialysate flow path" and "controlled compliant solution flow path" refer to flow paths operating within a controlled compliant system having the characteristic of controlled compliance, or of being controlled compliant as defined herein.

A "control pump" is means capable of moving fluid through a system at a specific rate. The term "control pump," can include for example an "ultrafiltrate pump," which is a pump that is operable to pump fluid bi-directionally to actively control the transfer of fluid volume into or out of a compartment or circuit.

A "control system" consists of combinations of components that act together to maintain a system to a desired set of performance specifications. The control system can use processors, memory and computer components configured to interoperate to maintain the desired performance specifications. It can also include fluid or gas control components and solute control components as known within the art to maintain the performance specifications.

A "control valve" is a valve for controlling the movement of a liquid or a gas. When the control valve directs the movement of gas, the "control valve" can open or close to regulate the movement of gas from a high pressure gas source to a lower pressure.

A "controller," "control unit," "processor," or "microprocessor" is a device which monitors and affects the operational conditions of a given system. The operational conditions are typically referred to as output variables of the system wherein the output variables can be affected by adjusting certain input variables.

A "degasser" is a component that is capable of removing dissolved and undissolved gasses from fluids.

The term "detachable" or "detached" relates to any component of the present invention that can be separated from a system, module, cartridge or any component of the invention. "Detachable" can also refer to a component that can be taken out of a larger system with minimal time or effort. In certain instances, the components can be detached with minimal time or effort, but in other instances can require additional effort. The detached component can be optionally reattached to the system, module, cartridge or other component. A detachable module can often be part of a reusable module.

"Dialysate" is the fluid that passes through the dialyzer and does not pass through the membrane into the blood flow.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid. The term "dialyzer" refers to a cartridge or container with two flow paths separated by semi-permeable membranes. One flow path is for blood and one flow path is for dialysate. The membranes can be in the form of hollow fibers, flat sheets, or spiral wound or other conventional forms known to those of skill in the art. Membranes can be selected from the following materials of polysulfone, polyethersulfone, poly(methyl methacrylate), modified cellulose, or other materials known to those skilled in the art.

"Disposable" refers to a component that is to be removed from the system and not reused.

The term "extracorporeal," as used herein generally means situated or occurring outside the body.

The term "extracorporeal circuit" or "extracorporeal flow path" refers to a fluid pathway incorporating one or more components such as but not limited to conduits, valves, pumps, fluid connection ports or sensing devices configured therein such that the pathway conveys blood from a subject to an apparatus for hemodialysis, hemofiltration, hemodiafiltration or ultrafiltration and back to the subject.

The terms "extracorporeal flow path pump" and "blood pump" refer to a device to move or convey fluid through an extracorporeal circuit. The pump may be of any type suitable for pumping blood, including those known to persons of skill in the art, for example peristaltic pumps, tubing pumps, diaphragm pumps, centrifugal pumps, and shuttle pumps.

"Flow" refers to the movement of a liquid or gas.

A "flow sensing apparatus" or "flow measuring apparatus" is an apparatus capable of measuring the flow of liquid or gas within a specific area.

A "fluid" is a liquid substance.

The term "fluid communication" refers to the ability of fluid or gas to move from one component or compartment to another within a system or the state of being connected, such that fluid or gas can move by pressure differences from one portion that is connected to another portion.

The term "fluidly connectable" refers to the ability of providing for the passage of fluid or gas from one point to another point. The two points can be within or between any one or more of compartments, modules, systems, components, and rechargers, all of any type.

"Infusate" is a solution of one or more salts for the adjustment of the composition of a dialysate.

The term "in-line" refers to a state in which a module or set of modules is fluidly connected to a dialysis machine, dialysis flow path or dialysis circuit. Dialysis can be on-going, paused or stopped during the in-line state wherein in-line only refers to the state of the modules being fluidly connected to the dialysis machine, dialysis flow path or dialysis circuit.

"Module" refers to a discreet component of a system. Each of the modules can be fitted to each other to form a system of two or more modules. Once fitted together, the modules can be in fluid connection and resist inadvertent disconnection. A single module can represent a cartridge to be fitted to a device or mechanism if the module is designed to contain all the necessary components for an intended purpose such as a sorbent for use in dialysis. In such a case, the module can be comprised of one or more compartments within the module. Alternatively, two or more modules can form a cartridge to be fitted to a device or mechanism where each module individually carries separate components but only when connected together contain in summation all the necessary components for an intended purpose such as a sorbent for use in dialysis. A module can be referred to as a "first module," "second module," "third module," etc. to refer to any number of modules. It will be understood that the designation of "first," "second," "third," etc. does not refer to the respective placement of the module in the direction of fluid or gas flow, and merely serves to distinguish one module from another unless otherwise indicated.

The term "non-reusable" refers to a component that cannot be reused in the component's current state. In certain instances, the term non-reusable can include the concept of being disposable, but is not necessarily limited to just being disposable.

The term "off-line" refers to a state in which a module or set of modules is fluidly disconnected from a dialysis machine, dialysis flow path or dialysis circuit. Dialysis can be on-going, paused or stopped during the off-line state wherein off-line only refers to the state of the modules being fluidly disconnected from the dialysis machine, dialysis flow path or dialysis circuit. The off-line state can also include a process whereby the module or set of modules is being recharged as defined herein.

An "operational line" or "line" is a passageway, conduit or connector that directs fluid or gas in a path used while the system is in operation.

The terms "pathway," "conveyance pathway," "fluid flow path," and "flow path" refer to the route through which a fluid or gas, such as dialysate or blood travels, or the route a gas travels.

A "photocell" is a sensor capable of measuring light or other electromagnetic radiation.

The terms "pressure meter" and "pressure sensor" refer to a device for measuring the pressure of a gas or liquid in a vessel or container.

A "pressure valve" is a valve wherein, if the pressure of the fluid or gas passing the valve reaches a certain level, the valve will open to allow fluid or gas to pass through.

The term "pump" refers to any device that causes the movement of fluids or gases by the application of suction or pressure.

A "push-on fitting" is a fitting for connecting two components wherein the components may be connected by applying pressure to the base of the fitting attached to the components.

A "quick connect fitting" is a fitting for connecting two components wherein the male portion of the fitting contains flexible flanges extending outward with a portion on the end of the flange extending further outward, and the female portion of the fitting contains an internal ridge so that when connected, the outward extending portion of the flange sits under the ridge. By applying pressure, the flexible flange can be forced inward, past the ridge, enabling easy removal.

A "recharger" is a component that is capable of recharging spent sorbent material to or near its original state. A recharger may be part of the dialysis system or may be separate from the rest of the system. If the recharger is separate from the rest of the dialysis system, the term may include a separate facility where the spent sorbent material is sent to be returned to, or near, its original state. A "recharger connector" or "recharger node" is a connector that fluidly connects a recharger to another component.

"Recharging" refers to the process of treating spent sorbent material so as to put the sorbent material back in condition for use in sorbent dialysis. Upon a sorbent material undergoing "recharging," the sorbent material can then be said to be "recharged." The term "recyclable" refers to material that can be reused.

"Reusable" refers in one instance to a material that can be used more than one time, possibly with treatment or recharging of the material between uses. Reusable may also refer to a cartridge that contains a material that can be recharged by recharging the material(s) contained within the cartridge.

A "sensor" is a component capable of determining the states of one or more variables in a system.

"Sorbent cartridge" refers to a cartridge that can contain one or more sorbent materials. The cartridge can be connected to a dialysis flow path. The sorbent materials in the sorbent cartridge are used for removing specific solutes from solution, such as urea. The sorbent cartridge can have a single compartmental design wherein all sorbent materials necessary for performing dialysis are contained within the single compartment. Alternatively, the sorbent cartridge can have a modular design wherein the sorbent materials are dispersed across at least two different modules, which can be connected to form a unitary body. Once the at least two modules are connected together, the connected modules can be referred to as a sorbent cartridge, which can be fitted to a device or mechanism. It will be understood that when a single module contains all the sorbent materials necessary for performing dialysis, the single module can be referred to as a sorbent cartridge.

"Sorbent materials" are materials capable of removing specific solutes from solution, such as urea.

"Spent dialysate" is a dialysate contacted with blood through a dialysis membrane and contains one or more impurity, or waste species, or waste substance, such as urea.

The term "substantially inflexible volume" refers to a three-dimensional space within a vessel or container that can accommodate a maximum amount of non-compressible fluid and resists the addition of any volume of fluid above the maximum amount. The presence of a volume of fluid less than the maximum amount will fail to completely fill the vessel or container. Once a substantially inflexible volume has been filled with a fluid, removal of fluid from that volume will create a negative pressure that resists fluid removal unless fluid is added and removed simultaneously at substantially equal rates. Those skilled in the art will recognize that a minimal amount of expansion or contraction of the vessel or container can occur in a substantially inflexible volume; however, addition or subtraction of a significant volume of fluid over the maximum or minimum will be resisted.

"Tap water" refers to water obtained through piping from a water supply without additional treatment.

A "threaded fitting" is a fitting for connecting two components wherein the male portion has a helical ridge wrapped around a cylinder, and the female portion is a cylindrical hole with internal helical ridges so that when the male portion is screwed into the female portion the two components are locked together.

A "twist-lock fitting" is a fitting for connecting two components wherein the male portion of the fitting contains a head with a length exceeding its width, the female portion of the fitting is a hole with a length that exceeds its width and is larger than the male portion, so that when the male portion is inserted into the female portion and either portion is twisted the two components become locked together.

"Uremic toxins" are toxins carried in the blood supply normally removed in the kidneys.

A "valve" is a device capable of directing the flow of fluid or gas by opening, closing or obstructing one or more pathways to allow the fluid or gas to travel in a particular path. One or more valves configured to accomplish a desired flow can be configured into a "valve assembly."

A "wash line" is a line that directs fluid between a recharger and a module.

The term "waste fluid" refers to any fluid that does not have a present use in the operation of the system. Non-limiting examples of waste fluids include ultrafiltrate, or fluid volume that has been removed from a subject undergoing a treatment, and fluids that are drained or flushed from a reservoir, conduit or component of the system.

The term "water source" refers to a source from which potable or not potable water can be obtained.

The term "waste species," "waste products," "waste," or "impurity species" refer to any molecular or ionic species originating from the patient or subject, including metabolic wastes, molecular or ionic species including nitrogen or sulfur atoms, mid-weight uremic wastes and nitrogenous waste. Waste species are kept within a specific homeostasis range by individuals with a healthy renal system.

Sorbent Dialysis

Sorbent dialysis allows dialysis with a small volume of dialysate, creating many advantages. In sorbent dialysis, spent dialysate, containing toxins removed from the blood of the patient, is passed through a sorbent cartridge. The sorbent cartridge of the invention can contain sorbent materials that selectively remove specific toxins from the spent dialysate, either completely or by replacing them with non-toxic material. This process converts the spent dialysate into clean dialysate, which is then redirected back to the dialyzer.

Modular sorbent cartridges, wherein each module contains select sorbent materials, can be useful in sorbent dialysis. This modular design critically allows for certain portions of the sorbent cartridge to be discarded, refilled, recycled or recharged. In certain embodiments, the sorbent materials can be structured into layers and/or intermixed. In particular, the modules can have the sorbent materials either intermixed or in layers wherein any combination of intermixed and layered modules can be used interchangeably together.

To save costs and waste, the modules of the modular sorbent cartridge may be rechargeable. The sorbent cartridges can be reusable or non-reusable, unless specifically specified as reusable. The sorbent material within the module can be recharged and made reusable by passing a solution containing the proper solutes through the layers of the sorbent module.

One non-limiting exemplary sorbent cartridge is shown in FIG. 1. Spent dialysate or fluid can flow from the bottom of the sorbent cartridge 1 to the top of the cartridge. The first sorbent material the spent dialysate (or fluid) contacts can be activated carbon 2. Activated carbon will remove nonionic toxins from the fluid by adsorption. Creatinine, glucose, uric acid, β2-microglobulin and other non-ionic toxins, except urea, can be adsorbed onto the activated carbon, removing those toxins from the fluid. Other non-ionic toxins will also be removed by the activated carbon. The dialysate (or fluid) then continues through the sorbent cartridge to the hydrous zirconium oxide layer 3. The hydrous zirconium oxide layer 3 can remove phosphate and fluoride anions, exchanging them for acetate anions. The fluid can continue to move through the sorbent cartridge into the alumina/urease layer 4. Urease can catalyze the reaction of urea to form ammonia and carbon dioxide. The result of this is the formation of ammonium carbonate. The phosphate anions present in the fluid can also be exchanged for hydroxide ions on the alumina. As the fluid continues through the sorbent cartridge, it reaches alumina layer 5. The alumina layer 5 can remove any remaining phosphate ions from the fluid and help retain urease within the sorbent cartridge, and in certain configurations this layer can exchange urea for ammonium and other components. The last layer through which the fluid travels can be the zirconium phosphate layer 6. In the zirconium phosphate layer 6, ammonium, calcium, potassium and magnesium cations can be exchanged for sodium and hydrogen cations. Ammonium, calcium, potassium and magnesium ions all preferentially bind to the zirconium phosphate, releasing the hydrogen and sodium ions originally present in the zirconium phosphate layer 6. The ratio of sodium to hydrogen ions released depends on the ratio originally present in the zirconium phosphate layer 6, and is therefore controllable. The result of the fluid passing through the sorbent cartridge 1 is that the fluid can be regenerated and form clean dialysate that can be safely passed back through a dialyzer to a patient. In any embodiment, potassium, calcium, and magnesium can be added to the clean dialysate to replace any ions which were removed by the sorbent cartridge. The ions can be added and/or controlled via an infusate system that can be positioned on a section of the fluid flow path after the sorbent cartridge.

Figure 2:
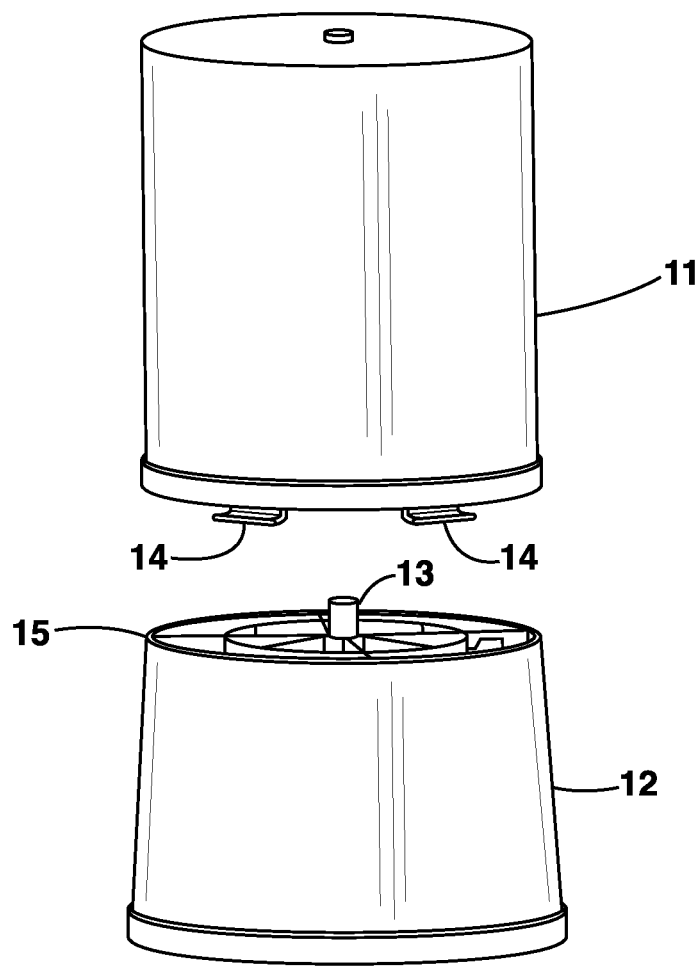
FIG. 2 shows a modular sorbent cartridge with two modules.

Given the cost of the sorbent cartridges and sorbent materials, it would be advantageous if parts of the cartridge could be reused or recharged. The present invention relates to a sorbent cartridge which includes at least one reusable module. As shown in FIG. 2, a reusable module 11 can be fluidly attached to a non-reusable module 12 by a connector 13 with the use of latches 14 disposed near the circumference of the reusable module 11. The latches 14 can be integrally formed as part of the reusable module 11, or non-reusable module 12. Alternatively, they may be a separate component that must be attached to the module 11. The latch members 14 can be mated to an annular connection ring 15 disposed on the circumference of module 12. One or more engagement members can be disposed inside the annular connection ring 15 to engage the latches 14 when positioned relative to each other using a radial motion. Such engagement can cause a rigid connection between the reusable module 11 and the non-reusable module 12. Other known locking or fastening mechanisms known to those of ordinary skill that can effectuate rapid and effective connections between two components are contemplated by the invention. Although only cylindrical modules are shown, it will be understood that modules of any shape such as rectangular, conical, triangular, etc. are contemplated by the present invention with a correspondent fastening mechanism. In certain embodiments, the connector 13 can be formed as part of the reusable module 11 and non-reusable module 12 and need not be a separate component that must be attached to the module 12. Rather, the connector 13 can be molded as part of the reusable module 11 and non-reusable module 12. The connector can be a combination of female and male connectors on a module. For example, a female connector can be disposed on one module, and a male connector on the other to form one connector 13 (not shown). In other embodiments, the connector can be affixed by mechanical means, glued or rigidly interfaced to the modules 11 and 12. In any embodiment, the connector 13 allows fluid to flow from the non-reusable module 12, through the connector 13, into the reusable module 11. Alternatively, the connector 13 is not a part of either the non-reusable module 12 or reusable module 11 but can be a separate component such as tubing. It will be understood that the connector 13 is defined in its broadest sense and encompasses any fluid connection between two points.

It will be understood that different combinations of reusable and non-reusable modules can be combined together. In certain embodiments, both modules may be reusable or both may be non-reusable. Moreover, any one of the modules can be detachable from each other or from a casing forming the body of the sorbent cartridge. The modules can be standardized components that are interchangeable with other modules and easily assembled. For example, the latches 14 in FIG. 2 allow for a simple, twist-lock between two modules. The twist lock allows for the modules to be connected to each other by an easy and rapid manual motion not requiring complex maneuvering of the modules. The connection, once made, can be resistant to inadvertent disengagement, but can also be readily disengaged when desired with a similar easy and rapid manual manipulation. For example, a force applied on the outside periphery of the modules near the latch, e.g. squeezing the module, can cause the latch member 14 to disengage from the engagement members. In other examples. The modules can be disengaged by simply rotation the modules relative to each other.

In certain embodiments, each module can function as a sorbent cartridge independently. In other embodiments, at least two modules can cooperate together when engaged to each other using, for example, the latches 14 in FIG. 2 and being fluidly connected together to function as a sorbent cartridge. The advantage of such a modular design as described herein is that different sorbent materials can be dispersed between the at least two modules to allow for any particular sorbent or combination of sorbent materials to be detachable from a sorbent cartridge.

In certain embodiments, the connector 13 can be formed as part of the reusable module 11 and non-reusable module 12 and need not be a separate component that must be attached to the module 12. Rather, the connector 13 can be molded as part of the reusable module 11 and non-reusable module 12. The connector can be a combination of female and male connectors on a module. For example, a female connector can be disposed on one module, and a male connector on the other to form one connector 13 (not shown). In other embodiments, the connector can be affixed by mechanical means, glued or rigidly interfaced to the modules 11 and 12. In any embodiment, the connector 13 allows fluid to flow from the non-reusable module 12, through the connector 13, into the reusable module 11. Alternatively, the connector 13 is not a part of either the non-reusable module 12 or reusable module 11 but can be a separate component such as tubing. It will be understood that the connector 13 is defined in its broadest sense and encompasses any fluid connection between two points.

In any embodiment, one or more fluid connectors can be arranged between any module of the invention, and one or more such fluid connectors can be provided in any of the described configurations herein. For example, a reusable or non-reusable module can have any number of connectors such as 1, 2, 3, 4, 5, or more. The spacing and distribution of the fluid connectors on the module can be positioned to enable and or increase flow of fluid between the modules. In one example, the fluid connectors can be spaced equidistant from each other or may be located axially or radially. The sorbent cartridge can also have one or more modules each having any number of fluid connectors. In contrast to known sorbent cartridges having a unitary design in which sorbent materials are arranged in layers without any connectors between such layers, the fluid connectors of the present invention allow for controlled fluid or gas flow to any particular sorbent or combination of sorbent materials. The fluid connectors also allow for any particular sorbent or combination of sorbent materials to be detachable from a sorbent cartridge. For example, a detachable module can be constructed with one or more sorbent materials. The detachable module can then be fluidly connected to the sorbent cartridge by fluid connectors. Such a configuration advantageously allows for separate treatment, recycling, or recharging of the sorbent or combination or mixture of sorbent materials not possible with known sorbent cartridges. In particular, known sorbent cartridges have all the sorbent materials being formed into layers or a plurality of sorbent materials being mixed without connectors in between such layers of one sorbent material, or mixtures of sorbent materials. It will be understood that the fluid connectors of the invention can be critical because the connectors control the order of sorbent materials to which a fluid or gas is exposed, the delivery of fluid or gas to a particular sorbent or combination of sorbent materials, and the flow and rate of flow of a fluid or gas to various sorbent materials, layers of sorbent materials, and combination or mixtures of sorbent material.

In one aspect of the invention, it will be understood that the present invention contemplates at least two modules that fit together, which is distinct from known dialysis systems having separate housings that do not form a unitary sorbent cartridge for ready attachment or insertion into a dialysis machine. A unitary sorbent cartridge of the present invention contains one or more of the sorbent materials described herein. In some embodiments, the cation and anion exchange materials necessarily reside in the sorbent cartridge. In other words, the cation and anion exchange resins (or other sorbent materials) are not separated into different housings outside a sorbent cartridge. Although the individual sorbent materials of the present invention may be separated into different detachable and/or reusable modules within the single sorbent cartridge wherein each module is connected by fluid connectors, the single sorbent cartridge design provides reduced size and weight that is not possible with the known dialysis systems having separate housings. The modules, as described herein, can also be further rigidly fixed to each other by latches and engagement members or any fixing or fastening mechanism known to those of ordinary skill in the art. Notably, the sorbent cartridge of the present invention can have all of the sorbent materials described herein including cation and anion exchange resins within a single unitary sorbent cartridge for convenient removal, service and monitoring. In particular, the sorbent cartridge can have a single compartmental design wherein all sorbent materials necessary for performing dialysis are contained within a single compartment. The sorbent cartridge can also have a modular design wherein the sorbent materials are dispersed across at least two different modules, which can be connected to form a unitary body. Once the at least two modules are connected together, the connected modules can form a sorbent cartridge to be fitted to a device or mechanism. Advantageously, the present sorbent cartridge can therefore be easier to recycle, recharge, dispose of, service and remove from a dialysis machine. In certain embodiments, the unitary design can also provide for a compact design that can be used in a portable dialysis machine. Further, manufacturability is benefited by the unitary design.

In any embodiment, the fluid connector can be a quick-connect, twist-lock fitting, push-on fitting, or threaded fitting. Other forms of such connection known to those of ordinary skill in the art are also contemplated by the present invention. Additionally, the connector can comprise a length of tubing and valve or a valve assembly. In certain embodiments, the connector can be manually assembled to connect any component or assembly of the invention. The connector can also be used to rigidly connect any one of the modules to a recharger as defined herein when a separate fastening mechanism is not provided.

Figure 24:
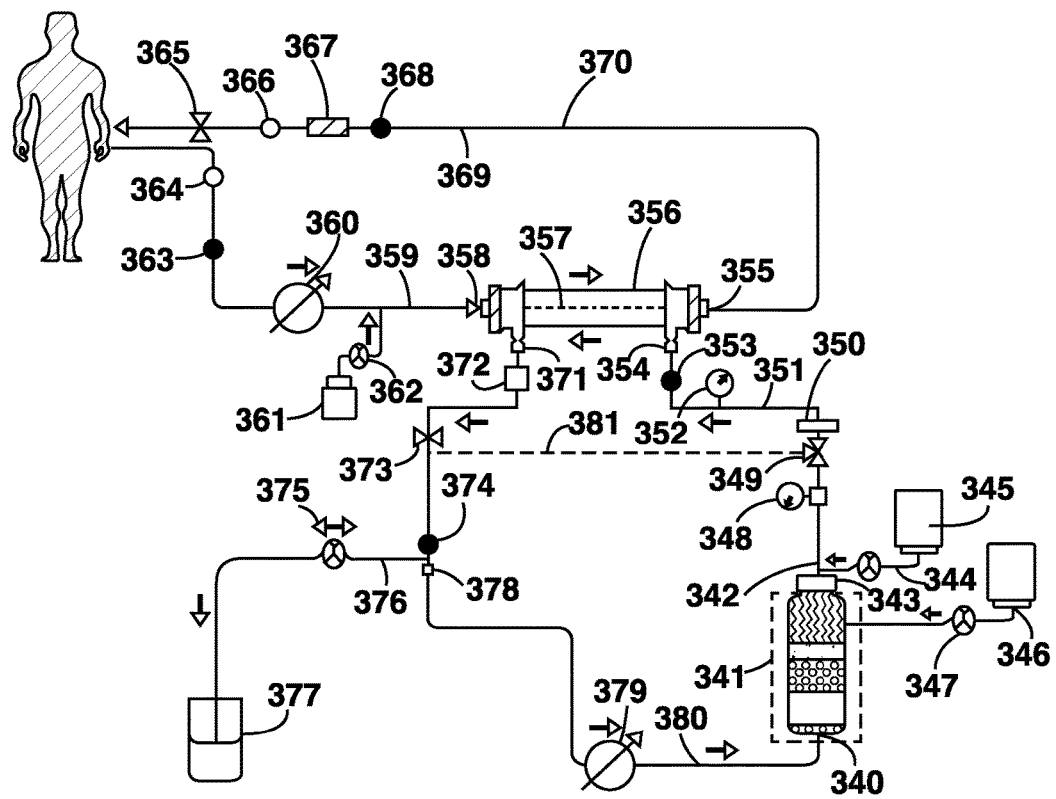
FIG. 24 shows a controlled compliant dialysis circuit utilizing a sorbent cartridge.

In any embodiment of the invention, at least one module can be in fluid communication with a controlled compliant dialysis circuit. A non-limiting example of a controlled compliant dialysis circuit is shown in FIG. 24. The patient's blood is circulated through an extracorporeal circuit 370. The portion of the extracorporeal circuit 370 that contains blood drawn from the patient can be referred to as the arterial line 359, which by convention is understood to mean a line for transporting blood from the patient regardless of whether blood is drawn from an artery or vein of the patient. Similarly, the portion that returns blood to the patient can be referred to as the venous line 369. In certain embodiments, the arterial line 359 and the venous line 369 connect with one or more veins of the patient. Locomotive power for moving the blood through the extracorporeal circuit 370 is provided by a blood pump 360, which is typically located along the arterial line 359. Valve 365 can be placed on venous line 369. Blood is typically conveyed through the extracorporeal circuit 370 at a rate of 50 to 600 mL/min and can be adjusted by a controller to any required rate suitable for a procedure performed by the invention. Blood pump 360 can be a peristaltic pump, although those skilled in the art will readily understand that other types of pumps can be used including diaphragm pumps, centrifugal pumps, and shuttle pumps. In certain embodiments, the blood pump 360 conveys blood through the dialyzer 356 where the blood is contacted with a blood side of a high permeability dialysis membrane 357. Blood enters the dialyzer 356 through a blood inlet 358 and exits through a blood outlet 355. The pressure of the blood prior to the blood pump 360 is measured by a pressure meter 363 and post dialyzer 356 by a pressure meter 368. The pressure at pressure meter 363 provides an indication of the adequacy of the blood flow into the circuit where increased vacuum is an indication of a less adequate access flow. The pressure indication at pressure meter 368 can serve to detect obstructions in the venous bloodline. Additional pressure meter 353 can be located after blood outlet 355. An air trap 367 is placed along the extracorporeal circuit 370 to prevent the introduction of air into the circulatory system of the patient. The air trap 367 is not limited to a particular design. Typical air traps employ a hydrophobic membrane that allows air to be separated from an air-liquid mixture by allowing air to pass through the membrane and retaining water-based fluids. Alternatively the air trap 367 can be run full, where a pressure meter can use a flexible impermeable membrane to transmit pressure pulses to a pressure transducer such that there is no direct air blood interface. Air-fluid detectors 364 and 366 are present to confirm that air is not present in the extracorporeal circuit 370, and additional air-fluid detector 374 can be present in the dialysis circuit 380. Air fluid detectors 364, 366 and 374 can be ultrasonic sensors that can detect a change in solution density or scattering due the presence of air or air bubbles.

During the course of conveyance of blood along the extracorporeal circuit 370, heparin or other anticoagulant is added to the blood to prevent clotting of blood within the dialyzer 356 or blood conveyance pathway/extracorporeal circuit 370. Heparin or another anticoagulant is added from an anticoagulant container 361 at a metered rate using an anticoagulant pump 362. The anticoagulant pump 362 can be any pump capable of accurately metering heparin.

Dialysate within the system is conveyed through one of a first dialysate pathway 351 in the dialysate circuit, which carries dialysate to the dialyzer 356, or a second bypass pathway 381 shown in a dashed line, which serves to bypass the dialyzer 356. The dialysis circuit can include a pair of quick connectors 378. The first and second pathways 351 and 351 have one or more conduits for conveying the dialysate. Access to the second bypass pathway 381 is controlled by valve 349. It is understood by one skilled in the art that three-way valve 349 can be replaced with a two-way valve or four-way valve with the same result to control the flow through the dialyzer 356 or bypass pathway 381. The first dialysate pathway 351, the second bypass pathway 381, and residual volume in the dialyzer 356 including conduits for conveying the dialysate together form a dialysis circuit 380 that houses the circulating volume of the dialysate present in the system. It is understood by one skilled in the art that three-way valve 349 could be replaced with two-way valves or four-way valves with the same result to control the flow through the dialyzer or bypass loop.

Dialysate that is conveyed through the dialyzer 356 on the dialysate side of the dialysis membrane 357 picks up waste products from the blood, including urea, by diffusion, hemofiltration or hemodiafiltration. Dialysate enters the dialyzer at a dialysate inlet end 354 and exits at an outlet end 371. The dialysate exiting the dialyzer 356 passes through a blood leak detector 372 that can determine the presence of blood in the dialysate indicating a breach in the dialysis membrane 357. Flow of dialysate from the dialyzer 356 can be stopped or controlled through the operation of valve 373 as well as to prevent the backup of dialysate into the dialyzer 356. The dialysate is conveyed through a sorbent cartridge 341 to remove waste products before being re-conveyed through the dialyzer 356. The dialysate enters the sorbent cartridge 341 at a dialysate inlet end 340 and exits at an outlet end 342. Refreshed dialysate exiting an outlet end 342 of the sorbent cartridge 341 can be monitored by a conductivity meter 348. Additional conductivity meter 352 can be present. Optionally, the dialysate can be filtered through a microbial filter 350. An air trap 343 can be positioned before or after outlet end 342 to remove gasses introduced into the dialysate by the sorbent cartridge 341. The volume of actively circulating dialysate is determined by the total void volume of the conduits and the sorbent cartridge 341 forming the dialysis circuit 380. The void volumes of the conduits and of the sorbent cartridge 341 forming the dialysis circuit 380 have a non-expandable or substantially inflexible volume.

The total void volume of the conduits having a substantially inflexible volume prevents the passive inflow and outflow of fluid volume due to pressure changes that can occur over the course of treatment. This results in a benefit because not all of the pressure changes during treatment are under precise control by a user or operator. A controlled compliance dialysis circuit is achieved by actively controlling the inflow (influx) and outflow (efflux) of fluid to and from the dialysis circuit 380 and the extracorporeal circuit 370. In this manner, the volume of fluid crossing the dialysate membrane 357 is under direct control and can be accurately determined.

The controlled compliance dialysis circuit can be accurately controlled to precisely remove or add fluid to the dialysis circuit. Due to the substantially inflexible void volume of the conduits, the sorbent cartridge 341 and other components of the dialysis circuit 380, the net movement of fluid over any time interval across the dialysate membrane can be accurately controlled by creating a means to accurately introduce or remove fluid from the patient. This capability is used to enhance the convective clearance of the system while controlling the net fluid removed from the patient.

As shown in FIG. 24, the dialysate is moved along the dialysis circuit 380 by a dialysate pump 379. When the control pump 375 is not operating, fluid along the length of the dialysis circuit 380 flows at a rate determined by the dialysate pump 379. When the control pump 375 is operating, fluid exiting the dialyzer 356 and traveling toward the conduit 376 is flowing at a rate that is the combination of the rates of the control pump 375 and the dialysate pump 379. However, the fluid traveling from the entry point of conduit 376 into the dialysis circuit 380 to the dialyzer 356 is traveling at the rate of the dialysate pump 379. As such, the rate of fluid traveling to the dialyzer 356 is not affected by the operation of the control pump 375. The dialysate pump can be operated at a rate from about 10 to about 400 mL/min, the specific rate being dependent on the rate of the blood pump 360 at the desired contact time with the dialysis membrane 357 to achieve diffusion of impurities from blood to the dialysate. The rate of the dialysate pump 379 and the blood pump 360 can be controlled by a controller (not shown).

Due to the substantially inflexible void volume of the conduits and the sorbent cartridge 341, bulk fluid or water is prevented from moving across the membrane 357 from the extracorporeal circuit 370 of the dialyzer 356 to the dialysate circuit 380 of the dialyzer 356. Specifically, due to the controlled compliant feature of the void volume of the dialysis circuit 380, water cannot passively move from the extracorporeal side to the dialysate side through the dialysis membrane. In the event of factors that tend to increase pressure on the extracorporeal side of the dialysis membrane, such as increased blood flow rate or blood viscosity, pressure across the membrane will automatically be equalized due to the limited volume of the dialysis circuit 380 and the non-compressible nature of the dialysate. In the event of factors that tend to increase pressure on the dialysate side of the dialysis membrane 357, such as increased dialysis flow rate, net movement of water from the dialysis circuit 380 to the extracorporeal circuit 370 is prevented by a vacuum that would form in the dialysate circuit 380 in the event of such a movement. Since the dialyzer can be a high flux type, there is some fluid flux back and forth across the dialyzer membrane due to the pressure differential on the blood and dialysate sides of the membrane. This is a localized phenomenon due to the low pressure required to move solution across the membrane and is called backfiltration, however results in no net fluid gain or loss by the patient.

Using the controlled compliance dialysis circuit described herein, net movement of water across the dialysis membrane occurs under active control rather than passively due to pressure differences that develop across the dialysis membrane due to normal operations. A control pump 375 is present and accesses the controlled compliance dialysis circuit 380 through a conduit 376. In certain embodiments, the conduit 376 joins with the controlled compliance dialysis circuit 380 at a point downstream from the dialyzer 356. The control pump 375 can be operated in an influx direction that moves fluid from a control reservoir 377 to the controlled compliance dialysis circuit 380 or in an efflux direction that moves fluid from the controlled compliance dialysis circuit 380 into the control reservoir 377. Due to the substantially inflexible volume of the dialysis circuit 380, volume added to the controlled compliance dialysis circuit when the control pump 375 operates in the influx direction causes net movement of fluid from the dialysate side of the dialysis membrane 357 to the extracorporeal side of the dialysis membrane 357. When the control pump 375 is operated in the efflux direction, fluid is drawn from the extracorporeal side of the dialysis membrane 357 into the controlled compliance dialysis circuit. In certain embodiments, the control pump 375 can be operated at a rate from 0 to about 500 mL/min in either direction.

An infusate pump 344 can be used to add a cation infusate 345 into the hemofiltration circuit 380 to generate a fluid having a proper physiological composition to serve as a replacement fluid for introduction into the extracorporeal circuit 370. A bicarbonate solution in a container 346 can further be added by a pump 347 to maintain a physiological pH in the fluid prior to introduction to the extracorporeal circuit.

It will be understood that the connector provides for a fluid connection in its broadest sense and can include any type of tubing, fluid or gas passageway, or conduit between any one or more components of the invention.

The sorbent material within the module can be recharged by passing a solution containing the proper solutes through the layers of the sorbent module. To recharge the sorbent modules in-line, the modules may be connected by wash lines to rechargers, which contain solutions for recharging the modules.

Figure 3:
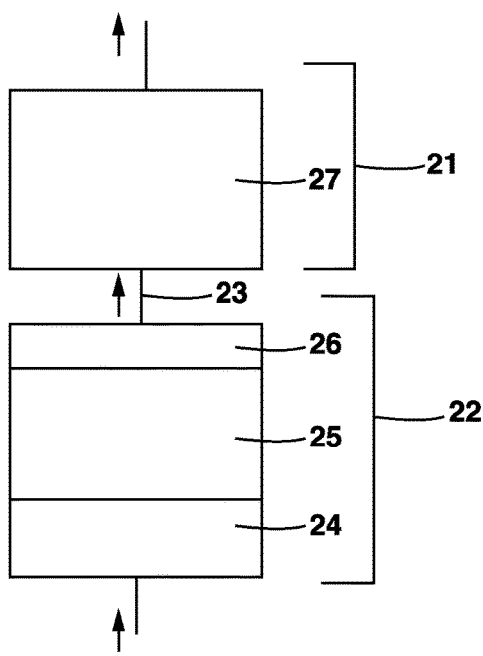
FIG. 3 shows a modular sorbent cartridge with two modules including activated carbon, alumina, urease, and zirconium oxide in the first module, which can be a reusable module, and zirconium phosphate in the second module, which can be a reusable module.

One embodiment of the modular sorbent cartridge is shown in FIG. 3. The non-reusable module 22 of the sorbent cartridge contains layers of activated carbon 24, alumina/urease 25, and hydrous zirconium oxide 26. The reusable module 21 contains zirconium phosphate 27. In certain embodiments, the term non-reusable can refer to the components in a cartridge, and in other embodiments, the term can refer to both the components in the cartridge and the cartridge itself.

After dialysis is complete, the zirconium phosphate layer 27 can contain ammonium, calcium, potassium and magnesium. The module 21 containing the zirconium phosphate may be removed, and the zirconium phosphate recharged. The reusable module can be disconnected from the connectors 23 connecting the reusable module to the non-reusable module, bypass line and/or wash line. The reusable module 21 is then removed from the modular sorbent cartridge. The module 21 can then be recharged, discarded and replaced, or alternatively, the sorbent material within the module can be removed and refilled. It will be understood that any one of the materials used in the present invention can be used multiple times. In such instances of multi-session use, the number of sessions in which one component can be used, can be the same or different from the number of sessions in which another component can be used. In one non-limiting example, a module containing urease may be used two times while another module containing zirconium phosphate can be used three times. In other cases, the module containing urease can be used three times, and the module containing zirconium phosphate used two times. It will be understood that there is no limitation on the numbers of uses for any multi-session use module as compared to another module used in the sorbent cartridge.

Figure 4:
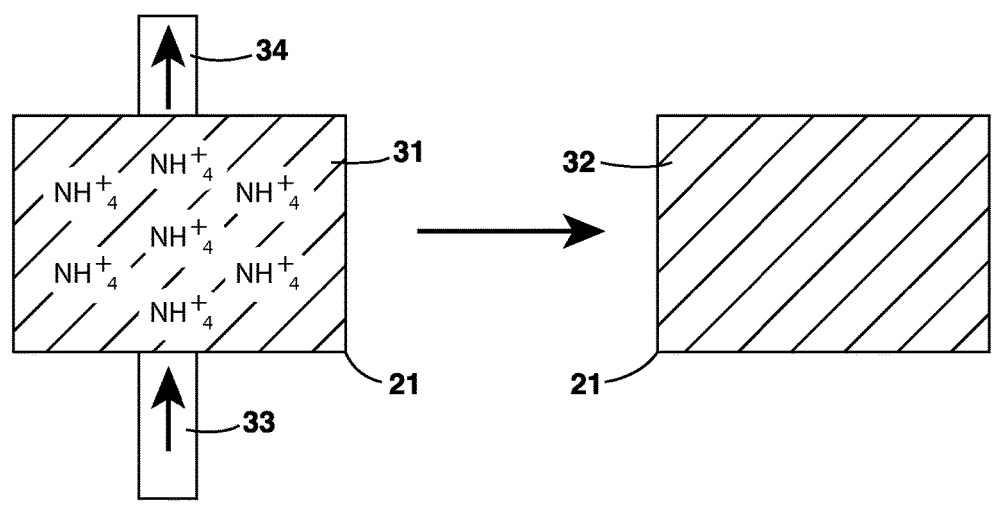
FIG. 4 shows a method for recharging the zirconium phosphate sorbent material.

A method of recharging the zirconium phosphate module is shown in FIG. 4. Wash fluid 33, containing sodium and hydrogen ions, can be passed through the reusable module 21, containing the used zirconium phosphate 31 with bound ammonium ions. This causes an exchange of ions, wherein hydrogen and sodium ions can replace the ammonium ions on the zirconium phosphate 31. The waste fluid 34 exiting the module 21 thus contains the freed ammonium ions, with excess sodium and hydrogen ions. This process creates a recharged zirconium phosphate layer 32, containing sodium and hydrogen ions for a subsequent dialysis. In certain embodiments, a recharger can be used to recharge spent sorbent material wherein the recharger contains fluid capable of restoring spent sorbent material to, or near, its original state or usable capacity.

Figure 5:
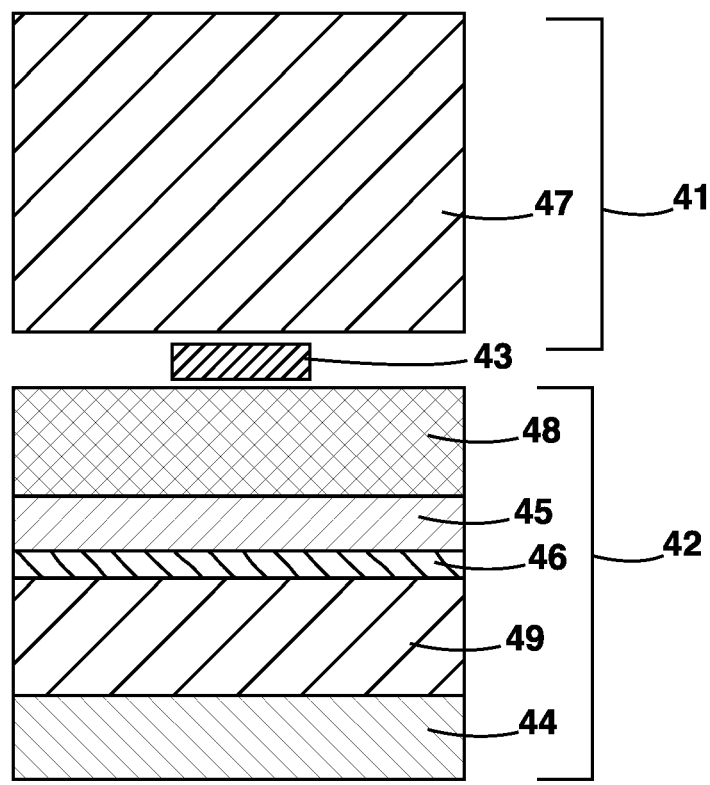
FIG. 5 shows a modular sorbent cartridge with two modules including activated carbon, zirconium phosphate, urease, alumina, and hydrous zirconium oxide in the first module, can be a reusable module, and zirconium phosphate in the second module.

Because calcium and magnesium ions may be more difficult to remove from the zirconium phosphate, and therefore the zirconium phosphate may be more difficult to recharge, it may be advantageous to remove the calcium and magnesium in the first, non-reusable module, so that none of those ions need to be removed in the reusable zirconium phosphate module. Such an embodiment is in FIG. 5. Spent dialysate enters the first, non-reusable module 42 where the spent dialysate can first flow through a layer of activated carbon 44 to remove non-ionic uremic toxins. The spent dialysate can then enter into a first layer of zirconium phosphate 49. The zirconium phosphate layer 49 can remove the calcium, magnesium and potassium from the fluid. Next the fluid can enter the hydrous zirconium oxide layer 46, which can remove the phosphate anions and exchange them with acetate anions. The fluid can then enter the urease layer 45 and alumina layer 48, where the urea can be converted to ammonium carbonate and any remaining phosphate ions can be removed. In other embodiments of the non-reusable module, any arrangement of the activated carbon, zirconium phosphate, hydrous zirconium oxide layer, and urease and alumina layer is contemplated. For example, the dialysate can first flow through a first layer of zirconium phosphate, activated carbon, then the hydrous zirconium oxide layer, and then enter the urease layer and alumina layer. Alternatively, the dialysate can first flow through the hydrous zirconium oxide layer, then a first layer of zirconium phosphate, the activated carbon, then enter the urease layer and alumina layer. Still further, the dialysate can first flow through the urease layer and alumina layer, then the hydrous zirconium oxide layer, then a first layer of zirconium phosphate, and then the activated carbon. The fluid can then flow through the connector 43, and into the second, reusable, sorbent module 41. The second sorbent module 41 can contain zirconium phosphate 47. Zirconium phosphate layer 47 can exchange the ammonium ions for sodium and hydrogen. Because the calcium, magnesium and potassium ions have already been removed by the first zirconium phosphate layer 49, this second layer 47 will not pick up those ions. After dialysis, the second module 41 will only contain zirconium phosphate bound to ammonium ions. As such, the sorbent material may be easier to recharge.

In embodiments where the reusable module contains zirconium phosphate and ion-exchange resin, or zirconium phosphate and hydrous zirconium oxide, the module may be recharged in the same manner. The activated carbon layer of a reusable module may be recharged by passing a heated water solution through the activated carbon layer. The alumina/urease layers can be recharged by first passing heated water, or the solutions described above for recharging zirconium phosphate, through the layer, and then passing a solution containing urease through alumina/urease layers.

Figure 6:
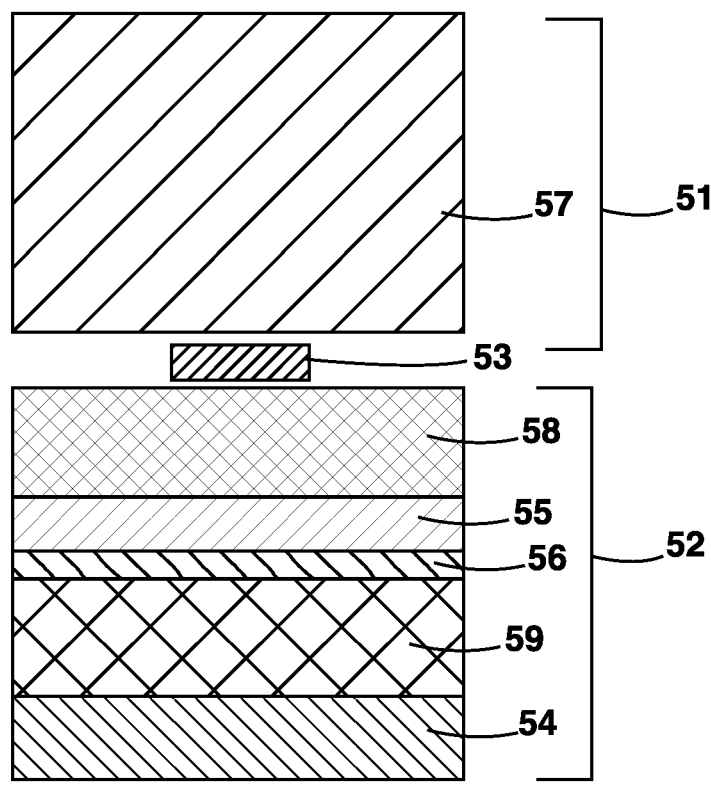
FIG. 6 shows a modular sorbent cartridge with two modules including activated carbon, ion exchange resin, alumina, urease, and hydrous zirconium oxide in the first module, which can be a reusable module, and zirconium phosphate in the second module.

Another non-limiting embodiment is shown in FIG. 6. Spent dialysate can enter the first, non-reusable, module 52 where it first flows through a layer of activated carbon 54 to remove non-ionic uremic toxins. The spent dialysate then enters into a layer of ion exchange resin 59. The ion-exchange resin layer 59 removes the calcium, magnesium and potassium from the fluid. Next the spent dialysate can enter the hydrous zirconium oxide layer 56, which removes the phosphate anions and exchanges them with acetate anions. The spent dialysate then enters the urease layer 55 and alumina layer 58, where the urea is converted to ammonium carbonate and any remaining phosphate ions are removed. In other embodiments of the first, non-reusable, module 52, any arrangement of the activated carbon, ion exchange resin, hydrous zirconium oxide layer, and urease and alumina layer is contemplated. For example, the dialysate can first flow through an ion exchange resin, activated carbon, then the hydrous zirconium oxide layer, and then enter the urease layer and alumina layer. Alternatively, the dialysate can first flow through the hydrous zirconium oxide layer, then the ion exchange resin, the activated carbon, then enter the urease layer and alumina layer. Still further, the dialysate can first flow through the urease layer and alumina layer, then the hydrous zirconium oxide layer, then the ion exchange resin, and then the activated carbon. The fluid can then flow through the connector 53, and into the second, reusable, sorbent module 51. The sorbent module 51 contains zirconium phosphate 57. The zirconium phosphate layer 57 can exchange the ammonium ions for sodium and hydrogen. Because the calcium, magnesium and potassium ions have already been removed by the ion-exchange resin layer 59, the zirconium phosphate layer 57 will not pick up those ions. Alternatively, the ion-exchange resin 59 may be selected to only remove the calcium and magnesium ions, such as by using a chelating ion exchange resin. This will allow use of less of the ion exchange resin. If such a resin is used, the potassium will be removed by the zirconium phosphate 57. Potassium is easier to remove from zirconium phosphate than calcium or magnesium. In other embodiments, the sorbent materials in each module may be intermixed as opposed to being arranged in layers.

One skilled in the art will recognize that different combinations of sorbent materials in both the reusable and non-reusable modules of the sorbent cartridge can be used without being beyond the scope of this invention. The sorbent materials described herein can be mixed together in any combination as shown in the specific embodiments of the invention.

Figure 7:
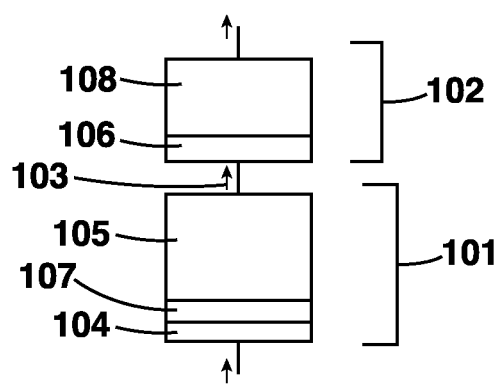
FIG. 7 shows a modular sorbent cartridge with two modules including activated carbon, alumina, urease, and zirconium phosphate in the first module, which can be a reusable module, and hydrous zirconium oxide and zirconium phosphate in the second module.

In any embodiment, the sorbent cartridge can be removed from a dialysis system. The sorbent cartridge once removed can be separated into one or more modules to be recharged, disposed of, or recycled. For example, FIG. 7 shows an embodiment wherein a second module 102 contains both hydrous zirconium oxide and zirconium phosphate. In certain embodiments, the second module 102 can be reusable as defined herein. The spent dialysate can enter the first module 101. The spent dialysate can first pass through an activated carbon layer 104. The spent dialysate can next pass through a first layer of zirconium phosphate 107, which removes the potassium, calcium and magnesium from the dialysate. Next the spent dialysate can move through the alumina/urease layer 105. In other embodiments of the first module, any arrangement of the activated carbon, zirconium phosphate, and urease and alumina layer is contemplated. For example, the fluid can first flow through activated carbon, then enter the urease layer, and then the zirconium phosphate. Alternatively, fluid can first flow through the zirconium phosphate layer, then activated carbon, and then enter the urease layer and alumina layer. Still further, the fluid can first flow through the urease layer and alumina layer, then the zirconium phosphate, and then the activated carbon. The fluid can then pass through the connector 103, and into the second module 102. The second module 102 contains a hydrous zirconium oxide layer 106, and a second zirconium phosphate layer 108, which removes the ammonium ions from the fluid. After dialysis, the reusable module 102 containing the hydrous zirconium oxide and zirconium phosphate can be recharged, discarded, or the sorbent material removed and new material added. In any embodiment, wash lines may be attached to connector 103 disposed on the reusable module 102 and a second connector positioned after the reusable module 102 wherein the second connector can be positioned thereon or as part of a fluid flow path (not shown).

Figure 8:
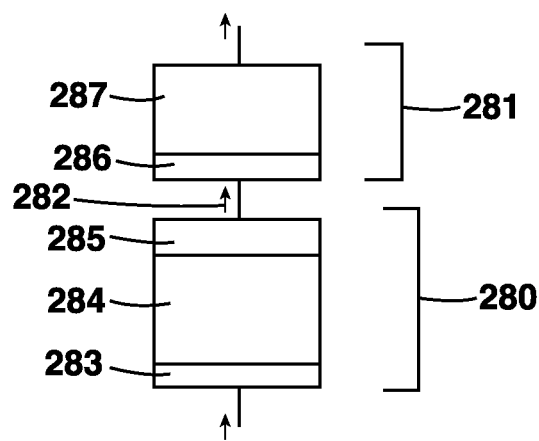
FIG. 8 shows a modular sorbent cartridge with two modules including activated carbon, alumina, urease, and hydrous zirconium oxide in the first module, which can be a reusable module, and ion exchange resin and zirconium phosphate in the second module.

Another non-limiting embodiment is shown in FIG. 8. Spent dialysate can enter the first, non-reusable, module 280 where it first flows through a layer of activated carbon 283 to remove non-ionic uremic toxins other than urea. The spent dialysate can then enter into a layer of alumina and urease 284, where the urea is converted to ammonium carbonate and phosphate ions are removed. Next the fluid can enter the hydrous zirconium oxide layer 285, which removes the remaining phosphate anions and exchanges them with acetate anions. In other embodiments of the first module, any arrangement of the activated carbon, hydrous zirconium oxide layer, and urease and alumina layer is contemplated. For example, the dialysate can first flow through an activated carbon layer, then the hydrous zirconium oxide layer, and then enter the urease layer and alumina layer. Alternatively, the dialysate can first flow through a hydrous zirconium oxide layer, then the activated carbon layer and then enter the urease layer and alumina layer. Still further, the dialysate can first flow through the urease and alumina layer, then the activated carbon layer, and then enter the hydrous zirconium oxide layer. The dialysate can first flow through a hydrous zirconium oxide layer, then through the alumina and urease layers, and then flow through the activated carbon layer. Alternatively the dialysate can first flow through the alumina and urease layer, then through the hydrous zirconium oxide layer, and then through the activated carbon layer. The fluid can then flow through the connector 282, and into the second, reusable, sorbent module 281. The sorbent module 281 contains an ion exchange resin layer 286, and a zirconium phosphate layer 287, which removes the ammonium ions from the fluid. In a different embodiment of the second module, the fluid can first pass through the zirconium phosphate layer and then the ion exchange resin. Alternatively, the sorbent materials in each module may be intermixed as opposed to being arranged in layers. After dialysis, the reusable module 281 containing the zirconium phosphate 287 and ion exchange resin 286 can be recharged, discarded, or the sorbent material removed and new material added. Alternatively, the sorbent materials in each module may be intermixed as opposed to being arranged in layers.

Figure 9:
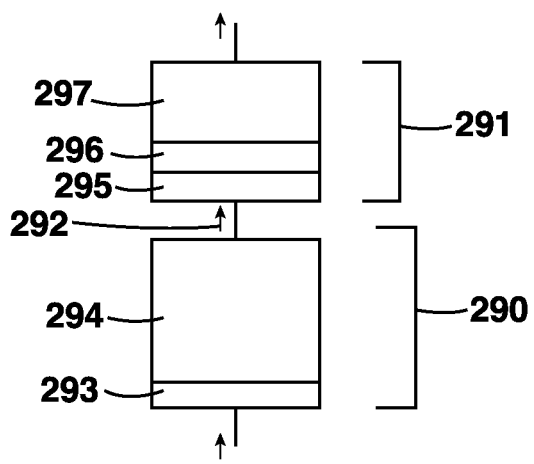
FIG. 9 shows a modular sorbent cartridge with two modules including activated carbon, alumina, and urease in the first module, which can be a reusable module, and hydrous zirconium oxide, ion exchange resin, and zirconium phosphate in the second module.

As in other embodiments, the hydrous zirconium oxide may be included in a second module as shown in FIG. 9. Spent dialysate can enter a first, non-reusable module 290 where it first flows through a layer of activated carbon 293 to remove non-ionic uremic toxins. The spent dialysate can then enter into a layer of alumina and urease 294, where the urea is converted to ammonium carbonate and phosphate ions are removed. In another embodiment of the first, non-reusable module 290, the dialysate can first flow through the alumina and urease, and then flow through the activated carbon. The fluid can then pass through connector 292 and into the second, reusable module 291. The second module 291 contains a layer of hydrous zirconium oxide 295, a layer of ion exchange resin 296 and a layer of zirconium phosphate 297. In other embodiments of the second module 291, any arrangement of the hydrous zirconium oxide, ion exchange resin and zirconium phosphate is contemplated. For example, the fluid may first pass through a layer of ion exchange resin, then pass through a layer of hydrous zirconium oxide and then pass through the zirconium phosphate. Alternatively, the fluid may first pass through the ion exchange resin, then pass through the zirconium phosphate and then through the hydrous zirconium oxide. Still further, the fluid may pass through the zirconium phosphate, then through the hydrous zirconium oxide, and then through the ion exchange resin. In another embodiment, the fluid can first pass through the hydrous zirconium oxide layer, then through the zirconium phosphate layer, and then through the ion exchange resin. Alternatively, the fluid can first pass through the zirconium phosphate layer, then the ion exchange resin, and then through the hydrous zirconium oxide layer. The sorbent materials in each module can also be intermixed as opposed to being arranged in layers.

Figure 10:
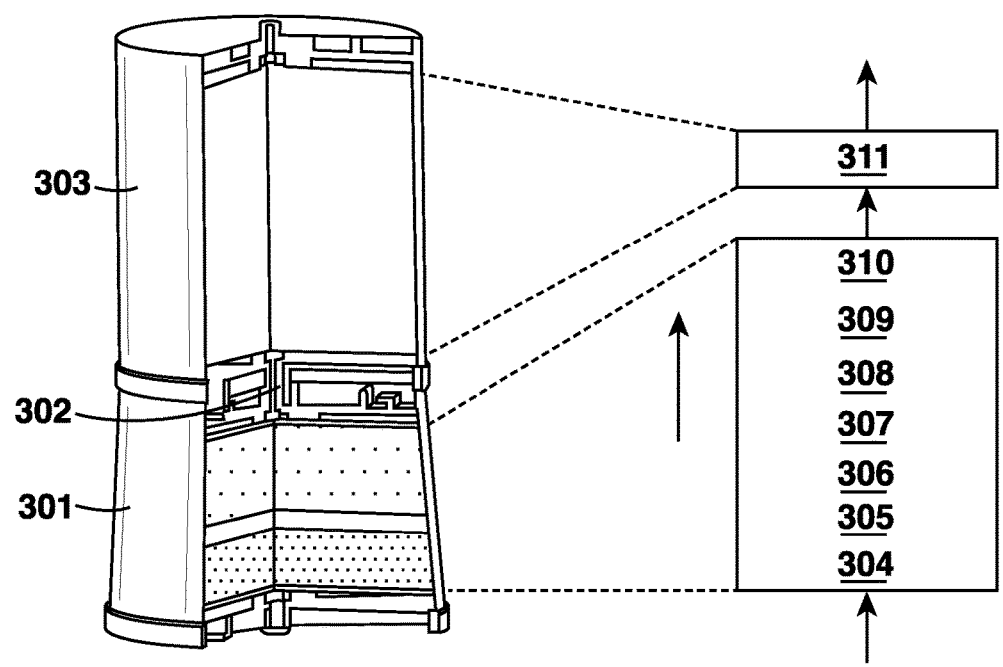
FIG. 10 shows a modular sorbent cartridge with two modules including sodium chloride/sodium bicarbonate, activated carbon, ion exchange resin, active jack bean meal (JBM)/alumina, alumina, hydrous zirconium oxide/glass beads, and sodium chloride in the first module, which can be a reusable module, and zirconium phosphate in the second module.

Another non-limiting embodiment is shown in FIG. 10. A layer of sodium chloride and sodium bicarbonate 304 are disposed on the first module 301. The sodium chloride and sodium bicarbonate will be dissolved as liquid enters the first module 301. Spent dialysate can enter a first module 301. In certain embodiments, the first module 301 can be reusable as defined herein. The spent dialysate can then enter a layer of activated carbon 305 to remove non-ionic uremic toxins. The spent dialysate can then enter into a layer of ion-exchange resin 306. In some embodiments, this can be a chelating ion exchange resin to selectively remove calcium and magnesium. The dialysate can then enter a layer of alumina and urease 307, where the urea is converted to ammonium carbonate and phosphate ions are removed. In some embodiments the urease can be in the form of urease active jack bean meal (JBM). The spent dialysate can next enter a layer of alumina 308. The fluid can then pass through a layer of hydrous zirconium oxide 309. In some embodiments, the hydrous zirconium oxide can be mixed with glass beads. A layer of sodium chloride 310 can be disposed on the end of first module 301, which will be dissolved by the fluid as it passes through the first module 301. The fluid then passes out of the first module 301, through the connector 302, and into the second module 303. In alternative embodiments of the first module 301, any arrangement of activated carbon, alumina, urease, ion exchange resin and hydrous zirconium oxide can be used. For example, the fluid can first pass through a layer of sodium chloride and sodium bicarbonate, then activated carbon, then hydrous zirconium oxide, then ion-exchange resin, then alumina and urease and then the sodium chloride. Alternatively, the fluid can first pass through a layer of sodium chloride, then ion-exchange resin, then activated carbon, then hydrous zirconium oxide, then alumina and urease, and then sodium chloride. The second module can contain zirconium phosphate 311, to remove the ammonium ions from solution. In some embodiments, the zirconium phosphate 311 can be mixed with glass beads.

One skilled in the art will realize that embodiments can be included that involve the sorbent materials being mixed within the module, as opposed to arranging the materials in layers. Such mixing of the sorbent materials can be performed interspersing the sorbent materials in a single layer by any method known to those of skill in the art. The arrangements include not just layers of sorbent materials, but also intermixed sorbent materials.

Figure 11:
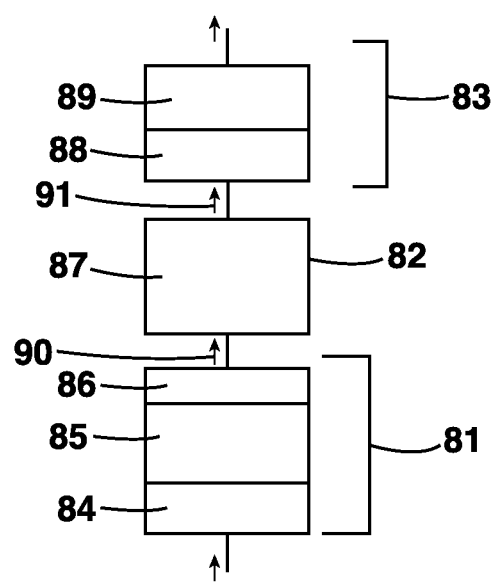
FIG. 11 shows a modular sorbent cartridge with three modules including activated carbon, alumina, urease, and hydrous zirconium oxide in the first module, which can be a reusable module, zirconium phosphate in the second module, and zirconium phosphate and activated carbon in the third module.

The modular sorbent cartridges in this invention are not limited to having two modules. Any number of modules may be utilized in this invention. A three module sorbent cartridge is shown in FIG. 11. The first module 81 contains a layer of activated carbon 84, a layer of alumina/urease 85, and a layer of hydrous zirconium oxide 86. In certain embodiments, any one of the first module 81 second module 82 or third module 83 can be reusable as defined herein. The described layers can also be mixed together rather than being provided in layers. In other embodiments of the first module of a three module sorbent cartridge, any arrangement of the activated carbon, hydrous zirconium oxide layer, and urease and alumina layer is contemplated. For example, the dialysate can first flow through activated carbon, then the hydrous zirconium oxide layer, and then enter the urease layer and alumina layer. Alternatively, the dialysate can first flow through the hydrous zirconium oxide layer, then the activated carbon, then enter the urease layer and alumina layer. Still further, the dialysate can first flow through the urease layer and alumina layer, then the hydrous zirconium oxide layer, and then the activated carbon. Again, the described arrangements include not just layers, but also intermixed sorbent materials. The fluid, after passing through these layers, can pass through a first connector 90, and into the second module 82. This second module 82 contains zirconium phosphate 87. The fluid can then pass through a second connector 91, and enter a third module 83. This third module 83 contains a second layer of zirconium phosphate 88, and a second layer of activated carbon 89 for final purification before passing out of the sorbent cartridge. In other embodiments of the third module 83 of a three module sorbent cartridge, any arrangement of the activated carbon and the second layer of zirconium phosphate are contemplated. For example, the dialysate can first flow through activated carbon and then the second layer of zirconium phosphate. It will be understood that any number of modules can be configured in the present invention. For example, a sorbent cartridge having four, five, six, seven, or more modules is contemplated by the invention. It will be understood that the described arrangements include not just layers, but also the sorbent materials being intermixed.

As each layer of sorbent material within the modular sorbent cartridge may be recharged, a cartridge is possible where all of the modules are reusable. It is still advantageous to utilize separate modules for the sorbent materials in order to direct the correct recharging solution through the correct module, and because different sorbent materials may need to be replaced more often than others.

Because the ability for the zirconium phosphate layer to bind ammonium ions is finite, while the capacity of the urease layer to break down urea into ammonia is not, it is possible that the capacity of the zirconium phosphate layer may be exceeded. In such a case, excess ammonium ions will be caused to pass through the sorbent cartridge and remain in the dialysate. To protect patient safety, once ammonia breakthrough has occurred, either the dialysis session can be stopped or at least urease can be prevented from catalyzing the conversion of urea to ammonia.

Figure 12:
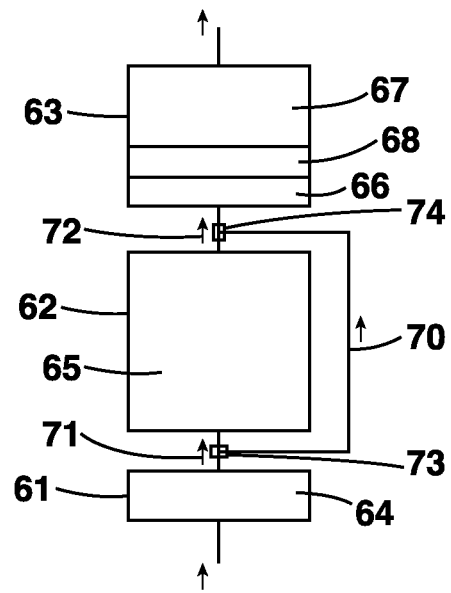
FIG. 12 shows a modular sorbent cartridge with three modules including activated carbon in the first module, which can be a reusable module, alumina and urease in the second module, and ion-exchange resin, zirconium phosphate, and hydrous zirconium oxide in the third module, with an optional bypass line to direct fluid from the first module, which can be a reusable module, to the third module.

FIG. 12 shows a three-module sorbent cartridge that can allow bypass of the alumina/urease layer in the case of ammonia breakthrough. Ammonia breakthrough can occur when the capacity of the zirconium phosphate layer to exchange ammonium ion is exceeded. In the event of ammonia breakthrough, the spent dialysate can enter the first module 61, which contains the activated carbon layer 64. In certain embodiments, any one of the first module 61, second module 62, or third module 63 can be reusable as defined herein. The spent dialysate then passes through a first connector 71, and by-pass flow valve 73. In normal operation, the flow valve 73 can be set to allow the fluid to pass into the second module 62. The second module 62 contains alumina/urease layer 65, which catalyzes the breakdown of urea into ammonium ions. In some embodiments, a single valve can be used and either first valve 73 or second valve 74 can be optional. For example, valve 74 can be optional wherein those skilled in the art will recognize that to alternately direct flow through second module 62 or bypass 70 can be accomplished by a configuring valve 73 as a 3-way valve. Other configurations to achieve the desired alternating direct flow are contemplated by the invention. The fluid then passes through the second connector 72, by the second valve 74, and into the third module 63. The third module 63 can contain a hydrous zirconium oxide layer 66, ion-exchange resin 68, and zirconium phosphate layer 67. In other embodiments of the third module 63 of a three module sorbent cartridge, any arrangement of the ion-exchange resin, hydrous zirconium oxide layer, and zirconium phosphate layer is contemplated. For example, the dialysate can first flow through ion-exchange resin, then the hydrous zirconium oxide layer, and then enter the zirconium phosphate layer. Alternatively, the dialysate can first flow through the hydrous zirconium oxide layer, then the ion-exchange resin, then enter the zirconium phosphate layer. Still further, the dialysate can first flow through the zirconium phosphate layer, then the hydrous zirconium oxide layer, and then the ion-exchange resin. Again, the described arrangements include not just layers, but also intermixed sorbent materials. After passing through the third module, the regenerated dialysate can exit the sorbent cartridge. In the event of ammonia breakthrough, the first valve 73 can be set to redirect the fluid into bypass line 70. This line will cause the fluid not to enter the second module 62, and therefore the urea will not be broken down into ammonia in the alumina/urease layer. The fluid will instead be directed to the second valve 74, which can be optional in certain embodiments, where the fluid enters the second connector 72, and then the third module 63. In this way dialysis may continue, while avoiding the creation of ammonia. In certain embodiments either the first valve 73 or the second valve 74 may be optional, and those of skill in the art will recognize that the function can be accomplished with only a single valve if either the first valve 73 or the second valve 74 is a 3-way valve. The valve or valve assembly may also include an access point for a sensor (not shown). The access point can be a portion of the valve assembly wherein a sensor can contact the fluid to take measurement data such as a flow or pressure reading. The form and construction of such access points contemplated by the present invention are those known to one of ordinary skill in the art. In an alternative embodiment, second valve 74 may be removed and the cartridge may still accomplish the bypass function.

Figure 13:
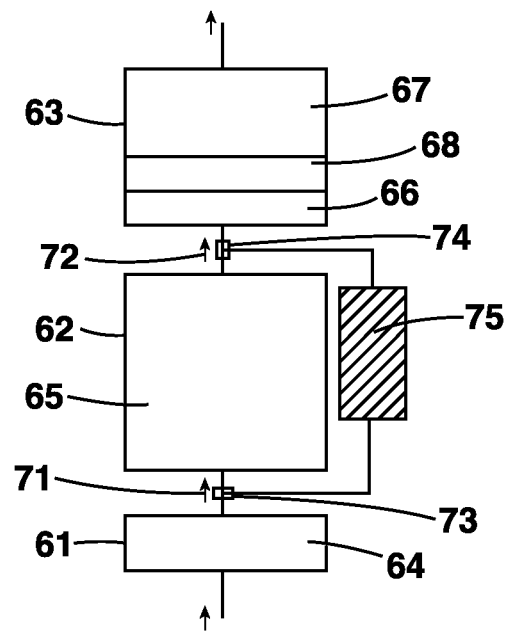
FIG. 13 shows a modular sorbent cartridge with three modules and with an optional bypass line connected to another component such as a recharger.

FIG. 13 shows an alternative embodiment to the sorbent cartridge shown in FIG. 12 wherein a first connector 71 and a flow valve 73 bypass flow through the second module 62 to a component 75. The component 75 can be a recharger used to recharge or clean the second module 62 while attached to the sorbent cartridge. In other embodiments, the component 75 can be a container storing a fluid such as a wash fluid or recharging fluid. In still other embodiments, the component 75 can be a pump for pumping fluid. Upon passing through the component 75, fluid can return through the second connector 72 via the second valve 74, which can be optional in certain embodiments, and into the third module 63. In some embodiments, the component 75 can be removed after a period of time and fluid allowed to flow from the third module 63 through the second connector 72 and the second valve 74, which can be optional in certain embodiments. The component 75 can be reversibly attached and detached as necessary. In certain embodiments either the first valve 73 or the second valve 74 may be optional, and those of skill in the art will recognize that a desired flow direction and function can be accomplished with only a single valve if either the first valve 73 or the second valve 74 is a 3-way valve. To recharge the sorbent modules in-line, the modules may be connected by wash lines to rechargers, which contain solutions for recharging the modules. As different sorbent materials will be recharging with different solutions, it is beneficial to have the fluid bypass one or more of the modules, and to pass through one or more of the modules.

Figure 14:
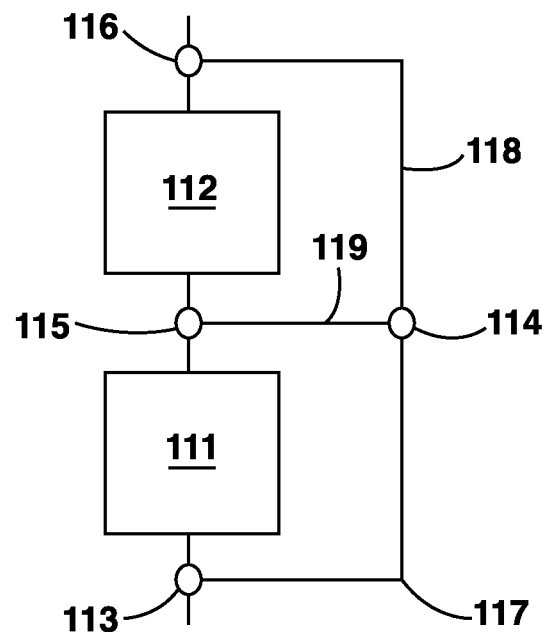
FIG. 14 shows a modular sorbent cartridge with two modules and two connected bypass lines to direct flow around either module.

FIG. 14 shows a configuration that may be utilized to allow fluid to selectively flow or not flow through each of the modules. Before entering the first module 111, the fluid can pass first valve 113. In certain embodiments, the first module 111 can be reusable as defined herein. The first valve 113 can either direct fluid into the first module 111, or into a first bypass line 117. If the fluid enters the bypass line 117, the fluid then passes to the second valve 114. The second valve 114 can direct fluid either through the second bypass line 118, or through the third bypass line 119 to the third valve 115, which is in between the two modules. In some embodiments, valve 114 can be optional wherein the bypass lines can function to move fluid around the modules. In other embodiments, valve 115 can be optional wherein the bypass lines can function to move fluid around the modules. Here, the fluid would be directed into the second module 112. Alternatively, if the fluid was directed through bypass line 118, then the fluid would go to fourth valve 116 and exit the portion of the system shown. Fluid that passes through the first module 111 also reaches third valve 115. Here, the third valve 115, which can be optional, may be set to direct fluid into the second module 112, or alternatively through the bypass line 119, which would bypass the second module 112. In this way, the valves can be set so that fluid is directed through both modules, either one of the modules, or none of the modules. Alternative embodiments with different valve arrangements are contemplated, for example those of skill in the art will recognize that the same bypass functionality can be accomplished with two valves if valves 116 and 113 are 3-way valves without valves 114 and 115 present.

Figure 15:
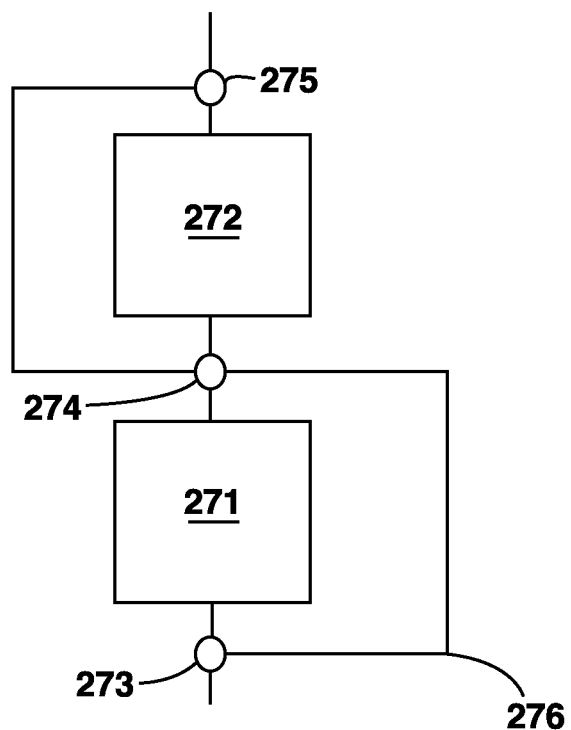
FIG. 15 shows a modular sorbent cartridge with two modules and a single bypass line to direct flow around either module.

An embodiment employing a single bypass line is shown in FIG. 15. Before entering the first module 271, fluid can pass through a first valve 273. In certain embodiments, the first module 271 can be reusable as defined herein. In other embodiments, the second module 272 can be reusable. First valve 273 can either direct fluid into the first module 271, or into a bypass line 276. If the fluid enters the bypass line 276, the fluid then passes to the second valve 274, bypassing the first module 271. Second valve 274 can direct fluid either through the bypass line 276, or into the second module 272. If the second valve 274 directs the fluid into the bypass line 276, the fluid passes to third valve 275, bypassing the second module 272. Alternative embodiments with different valve arrangements are contemplated, for example those of skill in the art will recognize that the same bypass functionality can be accomplished if valves 273 and 275 are 3-way valves without valve 274 present.

Figure 16:
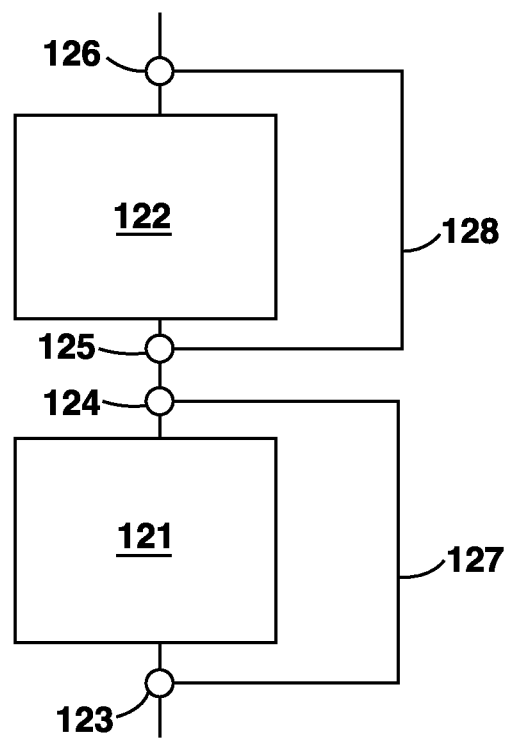
FIG. 16 shows a modular sorbent cartridge with two modules and two separate bypass lines to direct flow around either module.

Another embodiment, utilizing separate bypass lines for each module, is shown in FIG. 16. Before the fluid enters the first module 121, the fluid can pass through the first valve 123. In certain embodiments, the first module 121 can be reusable as defined herein. The first valve 123 can be set to either direct fluid into the first module 121, or redirect the fluid into a first bypass line 127 to second valve 124, which can be optional After passing through the first module 121 or bypassing the first module 121, the fluid next passes through the third valve 125, which can be optional. This third valve 125 can be set to either direct the fluid into the second module 122, or into a second bypass line 128 to the fourth valve 126. In this way the fluid can be made to flow through both modules, either module or none of the modules. Alternative embodiments with different valve arrangements are contemplated, for example those of skill in the art will recognize that the same bypass functionality can be accomplished if valves 126 and 123 are 3-way valves without valves 124 and 125 present.

In certain embodiments, the bypass lines can be formed or molded as part of the sorbent body casing. In this manner, the sorbent cartridge has a unitary body with the bypass lines being disposed thereon. One or more of the modules can be detachable from the unitary sorbent body cartridge having the bypass lines molded thereon. This design avoids the need for tubing or separate lines. In other embodiments, the connectors can form the bypass lines.

As demonstrated in FIGS. 14, 15, and 16, the precise number of valves or connectors utilized in any embodiment may be altered without being beyond the scope of the invention. Valves and connectors may be added or removed to any of the embodiments shown to accomplish the same end. Further, the functions of a four-way valve may be accomplished with two three-way valves or three two-way valves.

Figure 17:
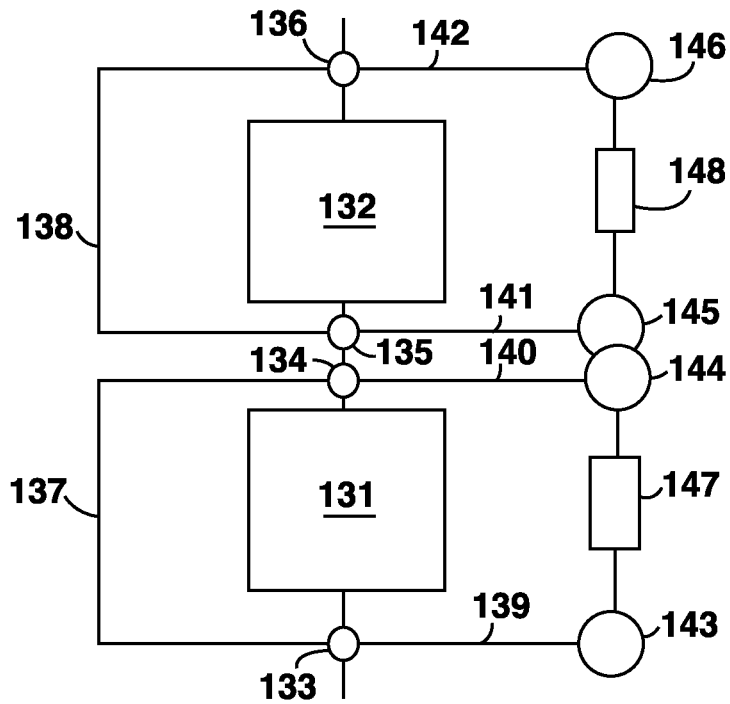
FIG. 17 shows a modular sorbent cartridge with two modules, two bypass lines and two rechargers.

The sorbent module may be connected to multiple rechargers and wash lines, so that multiple layers of sorbent material may be recharged without having to clean out the rechargers and lines and add new wash fluid. FIG. 17 shows an embodiment utilizing multiple wash lines, bypass lines and rechargers. The first recharger 147 can be connected to recharger nodes 143 and 144. A first wash line 139 can connect the first recharger node 143 to a first valve 133, which is positioned before the first module 131. In certain embodiments, the first module 131 can be reusable as defined herein. The first valve 133 can be set to direct the fluid into the first module 131, or alternatively to bypass the first module 131 through bypass line 137 which connects to a second valve 134 after the first module 131, or as a third alternative to direct fluid through the first wash line 139 to circulate between the first module 131 and the first recharger 147. The second recharger node 144 can be connected to this second valve 134 by a second wash line 140. Fluid flowing from the first bypass line 137 or from the first module 131 can flow through the second wash line 140 to the second recharger node 144 and then into the first recharger 147, or can pass to third valve 135, which can either direct the fluid into the second module 132, or alternatively to bypass the second module 132 through the second bypass line 138, which connects to the fourth valve 136 positioned after the second module. A third recharger node 145 can also be connected to the third valve 135 by third wash line 141, and can connect to a second recharger 148. The third valve 135 can direct fluid through the third wash line 141 to circulate between the second module 132 and second recharger 148, or alternatively through the second bypass line 138, or in the alternative to the second module 132. A fourth recharger node 146 can be attached by a fourth wash line 142 to the fourth valve 136. Fluid from the second module 132 or from the second bypass line 138 can selectively be directed through the fourth valve 136 into the fourth wash line 142 to the second recharger 148. Alternative embodiments with different valve arrangements are contemplated, for example those of skill in the art will recognize that the same bypass functionality can be accomplished for valve 133 represented by a configuration of 2-way valves separately on each of first bypass line 137, first wash line 139 and a connection to first module 131. Similarly, the same bypass functionality can be accomplished for valve 135 represented by a configuration of 2-way valves separately on each of second bypass line 138, second wash line 139 and a connection to second module 131 without valve 134 present. In an alternate embodiment, bypass lines 137 and 138, and wash lines 139 and 141 can be directly connected to the connectors between the modules, rather than to valves 134 and 136, and 133 and 135, respectively.

By utilizing the rechargers and bypass lines, different recharger fluids may be passed through the appropriate modules. The valves may be set open to the wash lines and closed to the connector, so that fluid is directed to the recharger. Alternatively, the first valve 133 may be set open to the wash line 139 and connector, while the second valve 134 is closed to the second module 132, so that fluid is made to circulate between the first module 131 and the recharger 147. If the first valve 133 is open to the bypass line 137, but closed to the connector, then fluid will be directed through the bypass line 137 around the first module 131. Finally, if the first valve 133 is open to the connector and the second valve 134 and third valve 135 are open to the second connector, the fluid will be directed through both modules.

Figure 18:
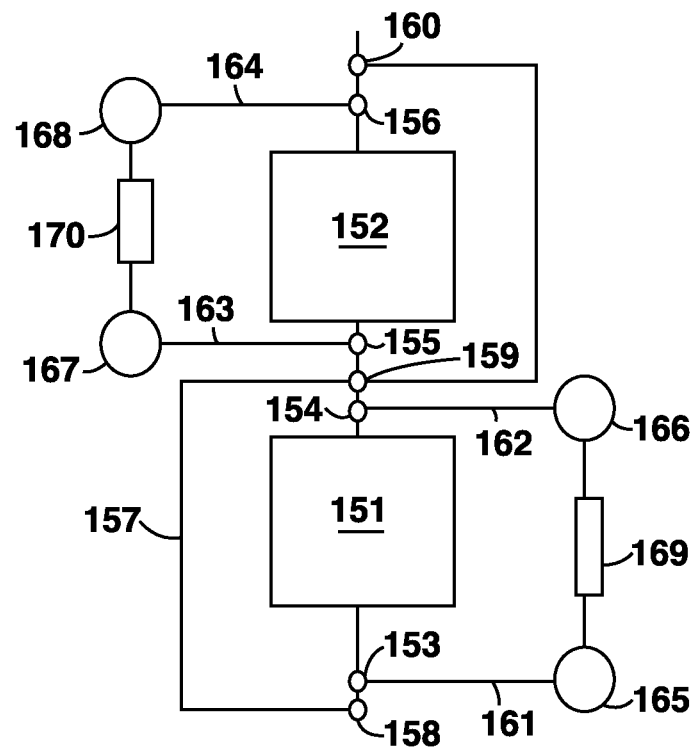
FIG. 18 shows a modular sorbent cartridge with two modules, a single bypass line to bypass either module, or two rechargers.

Another embodiment of the invention, utilizing a single bypass line, is shown in FIG. 18. The first recharger node 165 can be connected to a first valve 153, positioned before the first module 151, by a first wash line 161. In certain embodiments, the first module 151 can be reusable as defined herein. In other embodiments, the second module 152 can be reusable. A second recharger node 166 can be connected to a second valve 154, positioned after the first module 151, by a second wash line 162. The first recharger node 165 and second recharger node 166 can connect the first recharger 169. A third recharger node 167 can be connected to a third valve 155, positioned before the second module 152, by a third wash line 163. A fourth recharger node 168 can be connected to a fourth valve 156, positioned after the second module 152, by a fourth wash line 164. The third recharger node 167 and fourth recharger node 168 can connect the second recharger 170. A fifth valve 158, can be positioned before the first module 151, and connect to a bypass line 157, which directs fluid around the first module 151 to a sixth valve 159, positioned between the first and second modules, 151 and 152, respectively. The bypass line 157 can be further connected to a seventh valve 160, positioned after the second module 152. Other arrangements of valves are contemplated by the invention and those of skill in the art will recognize other combinations of valves that can be employed to accomplish these flow paths. For example, in some embodiments first valve 153, fourth valve 156 and sixth valve 159 can be optional and the flow path functions can be accomplished with four valves if fifth valve 158, second valve 154, third valve 155 and seventh valve 160 are three-way valves. The valves can be set to allow fluid to flow into the modules, through the bypass lines, or into the rechargers in several combinations.

Figure 19:
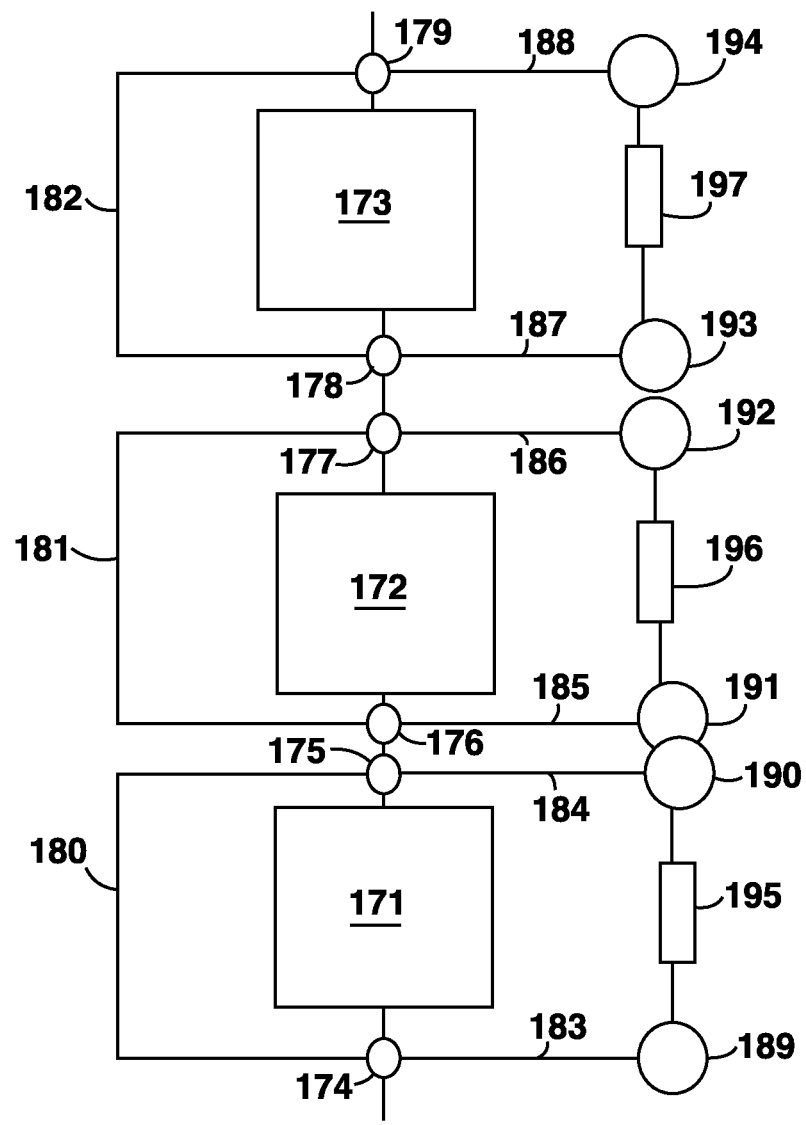
FIG. 19 shows a modular sorbent cartridge with three modules, three bypass lines and three rechargers.

One skilled in the art will recognize that this system is not limited to modular sorbent cartridges having two modules. Additional modules may be utilized with additional bypass lines and rechargers. FIG. 19 shows a three-module system for in-line module recharging. A first valve 174 can be connected to a first module 171, a first bypass line 180, and a first wash line 183. In certain embodiments, the first module 171 can be reusable as defined herein. The first wash line 183 is connected to a first recharger node 189. The first valve 174 may direct fluid into the first module 171 or into the first bypass line 180, which connects to a second valve 175 positioned after the first module 171. The second valve 175 can also be connected to a second wash line 184, and then to a second recharger node 190. The first recharger node 189 and second recharger node 190 can connect the first recharger 195. The fluid then travels to the third valve 176, positioned before the second module 172. The third valve 176 can be attached to a third wash line 185, which connects a third recharger node 191. This third valve 176 can direct fluid into the second module 172, or into a second bypass line 181, which connects to a fourth valve 177, positioned after the second module 172. This fourth valve 177 can also connect to a fourth wash line 186, which is connected to a fourth recharger node 192. The third recharger node 191 and fourth recharger node 192 can connect the second recharger 196. The fluid can then pass to a fifth valve 178, positioned before the third module 173. The fifth valve 178 can also be attached to a fifth wash line 187, which connects to a fifth recharger node 193. The fifth valve can direct the fluid into the third module 173, or into a third bypass line 182, which connects to a sixth valve 179, positioned after the third module 173. The sixth valve 179 can also be attached to a sixth wash line 188, which connects to a sixth recharger node 194. The fifth recharger node 193 and sixth recharger node 194 can connect the third recharger 197. The valves can be set to allow fluid to flow into the modules, through the bypass lines, or into the rechargers in several combinations. Further, additional valve arrangement known to those of ordinary skill are contemplated. In an alternate embodiment, bypass lines 180, 181 and 182, and wash lines 183, 185 and 187 can be directly connected to the connectors between the modules, rather than to valves 175, 177 and 179, and valves 174, 176 and 178, respectively.

Figure 20:
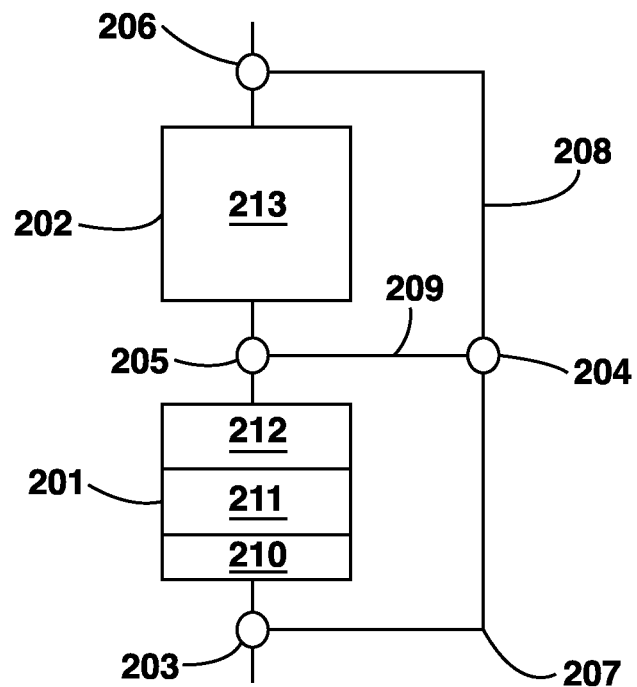
FIG. 20 shows a modular sorbent cartridge with two modules and two bypass lines to bypass the module, where the first module, which can be a reusable module, contains activated carbon, alumina, urease and hydrous zirconium oxide and the second module contains zirconium phosphate.

Various sorbent materials may be used in each of the modules of the sorbent cartridge. A non-limiting example is shown in FIG. 20. In certain embodiments, the first module 201 can be reusable as defined herein. In other embodiments, the second module 202 can be reusable. The first module 201 can contain layers of activated carbon 210, alumina/urease 211, and hydrous zirconium oxide 212. The second module 202 can contain zirconium phosphate 213.

After dialysis, the layers may be recharged in each module. Fluid capable of recharging activated carbon, hydrous zirconium oxide, and alumina/urease may be passed through the first valve 203, and into the first module 201. The fluid can then pass out of the first module 201 to second valve 205. This fluid may then be redirected around the second module 202 into bypass line 209. The fluid can pass to third valve 204, into third bypass line 208, and to the fourth valve 206, thus bypassing the second module 202. Alternatively, fluid for recharging zirconium phosphate 213 may be introduced. The fluid will pass to valve 203, and be redirected into bypass line 207 to third valve 204. The fluid may then be redirected through bypass line 209 to the second valve 205. Here the fluid will be directed to flow into the second module 202. This allows recharging and recycling of either module without introducing the recharging fluid into the other module. The sorbent materials within each module may be in any order. Alternatively, the sorbent materials within a module may be intermixed. Further, additional valve arrangements known to those of ordinary skill are contemplated.

Figure 21:
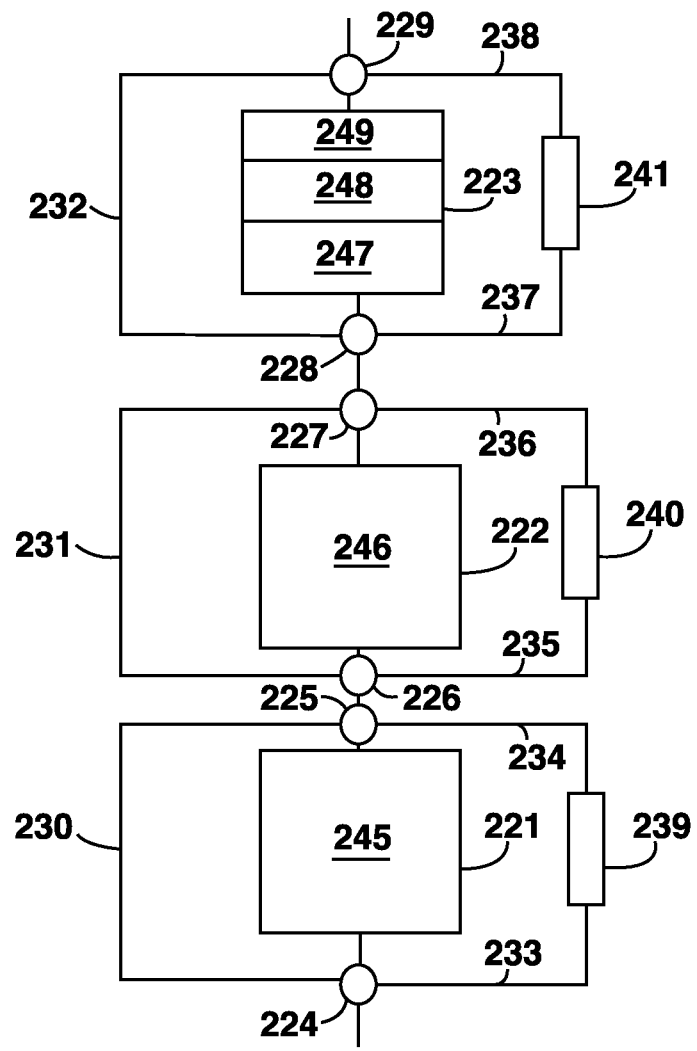
FIG. 21 shows a modular sorbent cartridge with three modules, three bypass lines, and three rechargers, wherein the first module, which can be a reusable module, contains activated carbon, the second module contains alumina and urease, and the third module contains hydrous zirconium oxide, ion-exchange resin and zirconium phosphate.

Another embodiment of the invention is the 3-module cartridge shown in FIG. 21. A first valve 224 can be connected to a first module 221, a first bypass line 230, and a first wash line 233. The wash line is connected to a first recharger 239. The first valve 224 may direct fluid into the first module 221 or into the first bypass line 230, which can connect to a second valve 225 positioned after the first module 221. The second valve 225 can also connect to a second wash line 234, and then to the first recharger 239. The fluid can then travel to the third valve 226, positioned before the second module 222. Third valve 226 can attach to a third wash line 235, which connects a second recharger 240. This third valve 226 can direct fluid into the second module 222, or into a second bypass line 231, which can connect to a fourth valve 227, positioned after the second module 222. The fourth valve 227 can also connect to a fourth wash line 236, which is connected to the second recharger 240. The fluid can then pass to a fifth valve 228, positioned before the third module 223. The fifth valve 228 can also attach to a fifth wash line 237, which connects to a third recharger 241. The fifth valve 228 can direct the fluid into the third module 223, or into a third bypass line 232, which connects to a sixth valve 229, positioned after the third module 223. The sixth valve 229 can also attach to a sixth wash line 238, which connects to the third recharger 241. The first module 221 can contain activated carbon 245. The second module 222 can contain alumina/urease 246. In certain embodiments, any one of the first module 221, second module 222, or third module 223 can be reusable as defined herein. The third module 223 can contain hydrous zirconium oxide 247, ion exchange resin 248, and zirconium phosphate 249. Further, additional valve arrangement known to those of ordinary skill are contemplated. In other embodiments of the third module of a three module sorbent cartridge, any arrangement of the ion-exchange resin, hydrous zirconium oxide layer, and zirconium phosphate layer is contemplated. For example, the dialysate can first flow through ion-exchange resin, then the hydrous zirconium oxide layer, and then enter the zirconium phosphate layer. Alternatively, the dialysate can first flow through the hydrous zirconium oxide layer, then the ion-exchange resin, then enter the zirconium phosphate layer. Still further, the dialysate can first flow through the zirconium phosphate layer, then the hydrous zirconium oxide layer, and then the ion-exchange resin. Again, the described arrangements include not just layers, but also intermixed sorbent materials.

After use, any of the spent modules may be discarded and replaced. They may also be recharged. The activated carbon 245 may be recharged by passing through the first module 221 a fluid of heated water. The alumina/urease 246 may be recharged by first passing a fluid of heated water through second module 222, and then passing a solution containing urease through. The third module 223, containing hydrous zirconium oxide 247, ion exchange resin 248, and zirconium phosphate 249 may be recharged by passing through the module a solution containing hydrogen and sodium ions. By selectively directing fluid through modules, or through the bypass lines, each of the modules may be recharged for further use. In an alternate embodiment, bypass lines 230, 231 and 232, and wash lines 233, 235 and 237 can be directly connected to the connectors between the modules, rather than to valves 225, 227 and 229, and 224, 226 and 228, respectively.

One skilled in the art will recognize that the precise order of sorbent materials within the modules, or the module in which a particular sorbent material is contained, may be modified without detracting from the invention. Various embodiments exist wherein the sorbent materials are arranged differently within the sorbent modules. Further, the sorbent materials may be mixed within the modules, as opposed to arranging the material in layers.

In all embodiments, one or more of the modules may also be made detachable. This will enable the detachment of one or more modules without detaching the others. The detached modules can be discarded and replaced, recharged, or the sorbent material may be discarded, the module refilled, and then re-used. To protect against cross-usage by patients, the detachable modules may be furnished with an identification component, such as a barcode. This will enable the same detachable module to be matched to a particular patient, and thereby avoid use of the module by another patient.

In order to ensure that all of the residual fluid is removed from the reusable modules, valves, bypass lines and wash lines, it may be advantageous to blow a gas, such as air, or an inert gas such as argon, through the module. In alternative embodiments, the gas may be air, filtered air, nitrogen, helium, or other gas. The wash line may be adapted so that a gas may be blown through the module instead of, or in addition to, a wash liquid.

Figure 22:
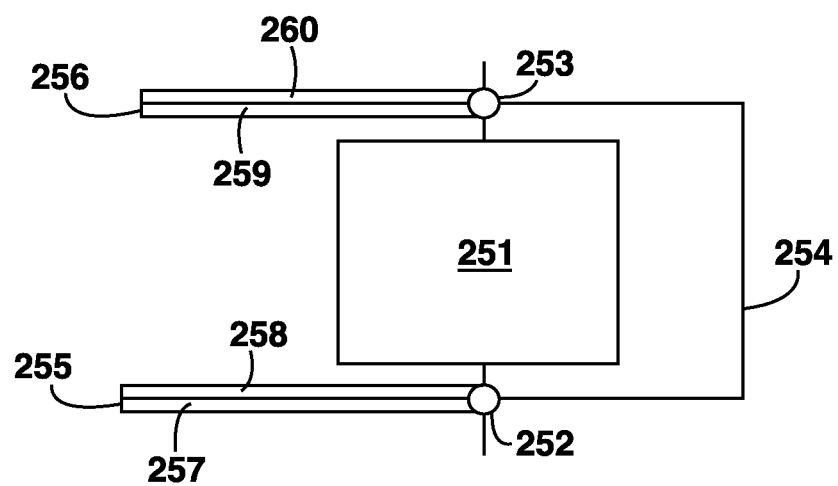
FIG. 22 shows a single module from a modular sorbent cartridge with a bypass line, and two wash lines each divided into gas and fluid wash lines.

Alternatively, a wash line may be divided into two lines as shown in FIG. 22. FIG. 22 shows a first module 251 from an embodiment similar to that shown in FIG. 17, wherein the wash line is adapted to utilize both a liquid and a gas. In certain embodiments, the first module 251 can be reusable as defined herein. The first wash line 255 can connect to a first valve 252 positioned before the first module 251. The first valve 252 can also connect to the first bypass line 254. The first bypass line 254 can direct either liquid or gas around the first module 251 to the second valve 253. The first wash line 255 can be further divided into two lines. These lines are the liquid wash line 257, and the gas wash line 258. A second wash line 256 can connect to the second valve 253, and also have both a liquid wash line 259 and a gas wash line 260. This embodiment allows both gas and liquid to pass either into the first module, or into the bypass line and around the first module. A second module, second bypass line, and third and fourth fluid lines are attached, so that fluid or gas may selectively be made to enter either module, or to bypass them.

Figure 23:
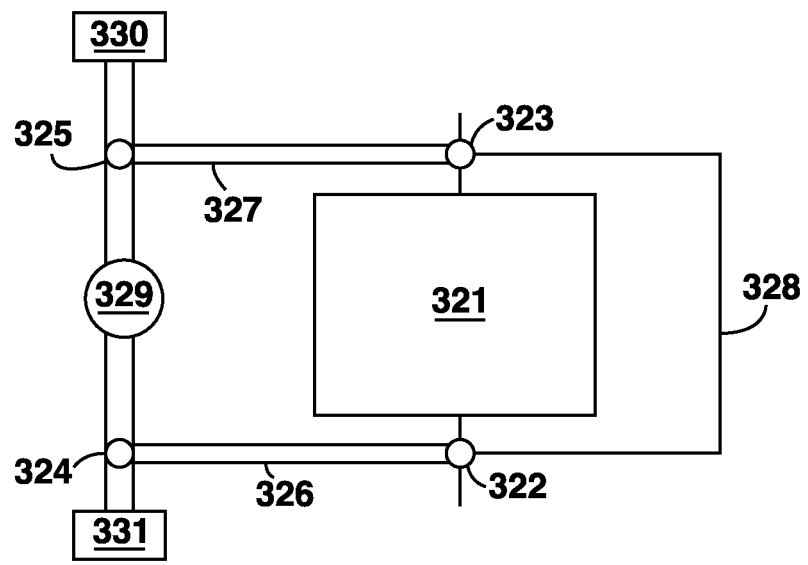
FIG. 23 shows a single module from a modular sorbent cartridge with a bypass line, a recharger, and two wash lines each divided into gas and fluid wash lines.

FIG. 23 shows an alternative embodiment utilizing both a gas and liquid line. The first wash line 326 can connect a first valve 324 to a second valve 322. The first valve 324 can be connected to the recharger connector 329, and a fluid collector 331. The recharger connector 329 can also be attached to third valve 325. Third valve 325 can connect the gas source 330 and fourth valve 323 via second wash line 327. Both the second valve 322 and the fourth valve 323 connect to the module 321 and a bypass line 328. This embodiment allows both gas and liquid to circulate through the module 321, or around the module.

In addition to dividing the wash line into a gas wash line and a liquid wash line, the wash line may be divided into two different liquid lines. This enables different liquids to travel between the recharger and the modules.

To make use of the modular sorbent cartridge easier, the valve or valve assembly may be operated by a programmable controller or computer system that can be programmed to regulate flow through the valves and into and out of the modules. An optical sensor, photocell or other flow sensing apparatus may detect the flow of fluid through any two points in the sorbent cartridge. For example, an optical fluid flow device can be provided for measuring flow wherein the device includes an optical fluid pressure measuring device having sensors positioned in any one of the flow paths between the modules, in the connectors, or in the valve assemblies. Preferably, the sensors will be placed in a passageway defined between the modules. In certain embodiments, the optical fluid sensors can be connected to an interferometer associated with an opto-electronic demodulator which has an output signal representing the differential pressure between the two sensed areas. In other embodiments, a flow sensing apparatus can have a flow-responsive element projecting into a fluid flow path, and a position sensor associated with the element which detects a change in position of the flow responsive element in response to the fluid flow. The flow-responsive element can be made of a wide variety of materials having the desired properties known to those of ordinary skill in the art.

It will be apparent to one skilled in the art that various combinations and/or modifications and variations can be made in the dialysis system depending upon the specific needs for operation. Moreover, features illustrated or described as being part of one embodiment may be used on another embodiment to yield a still further embodiment.

We claim:

1. A method of recharging a sorbent for dialysis, comprising the steps of:
connecting at least one reusable module containing either zirconium oxide or zirconium phosphate, and a second module in series with one or more connectors, wherein the reusable module and second module each contain one or more sorbent materials;
fluidly connecting at least one connector to at least one wash line, wherein the wash line is fluidly connected to a recharger;
fluidly connecting at least one connector to at least one bypass line, wherein the bypass line diverts flow from the connector to bypass at least one module;
connecting a valve assembly to the connectors at junctions between the modules, wash lines and/or bypass lines; the valve assembly including a first valve positioned on a connector; connecting the first valve to a wash line and a bypass line;
flowing spent dialysate through the reusable module and the second module; and
selectively opening and closing the valve assembly to direct flow from the recharger, through the wash line, and through at least the reusable module to recharge the zirconium oxide or zirconium phosphate.

2. The method of claim 1, selectively opening and closing the valve assembly wherein the first valve is open to the wash line, and closed to the second module and bypass line such that flow is directed from the recharger, through the wash line, and into the reusable module.

3. The method of claim 2, further comprising a second valve positioned on a connector between the reusable module and the second module; the second valve connecting the connector on which the second valve is positioned to a second wash line and a bypass line; selectively opening and closing the valve assembly wherein the second valve is open to the second wash line and reusable module, and closed to the second module and a bypass line, such that flow circulates between the recharger and the reusable module.

4. The method of claim 1, further comprising the first valve positioned on a first connector before a reusable module and a second valve positioned on a second connector between the reusable module and the second module; selectively opening and closing the valve assembly, wherein the first valve is open to the wash line and first connector, and closed to the bypass line such that flow circulates between the reusable module and the recharger, but wherein the second valve is closed such that flow cannot continue from the reusable module to the second module.

5. The method of claim 1, further comprising the first valve positioned on a connector before the reusable module, selectively opening and closing the valve assembly, wherein the first valve is open to the bypass line, and closed to the wash line and the connector, such that flow is directed through the bypass line to bypass the reusable module.

6. The method of claim 1, further comprising the first valve positioned on a connector before the reusable module, selectively opening and closing the valve assembly, wherein the first valve is open to the connector, and closed to the bypass and wash lines, such that flow is directed through the connector and through the reusable module.

7. The method of claim 1, further comprising a pump attached to the recharger or wash line.

8. The method of claim 1, further comprising an inert gas selected from any one of argon, air, filtered air, nitrogen, and helium to blow out the module.

9. The method of claim 1, wherein the wash lines are subdivided into a top and a bottom wash line.

10. The method of claim 9, wherein the top line is a fluid line and the bottom line is a gas line.

11. The method of claim 9, wherein the top line is a gas line and the bottom line is a fluid line.

12. The method of claim 9, wherein both the top line and the bottom line are fluid lines.

13. The method of claim 1, wherein at least one module further comprises one or more sorbent materials selected from the group consisting of activated carbon, alumina, urease and ion exchange resin.

14. The method of claim 1, wherein at least one of the reusable module and second module contain multiple sorbent materials.

15. The method of claim 1, wherein the reusable module and second module comprise a single sorbent cartridge.

16. The method of claim 15, wherein the reusable module is not detached from the sorbent cartridge before recharging.

17. The method of claim 1, wherein the second module is a reusable module.

18. The method of claim 17, further comprising:
fluidly connecting at least a second connector positioned between the reusable module and the second module to at least a second wash line, wherein the second wash line is fluidly connected to a second recharger;
fluidly connecting the second connector to a second bypass line, wherein the second bypass line diverts flow from the second connector to bypass at least one module;
connecting a second valve to the connectors at junctions between the modules, wash lines and/or bypass lines; and
selectively opening and closing the second valve to direct flow through the connectors, modules, wash lines and/or bypass lines.

19. The method of claim 18, wherein the one or more sorbent materials contained in the first reusable module are not identical to the one or more sorbent materials contained in the second module.

20. The method of claim 18, further comprising selectively opening and closing the first valve and the second valve such that flow is circulated between the first recharger and the first reusable module, and such that flow is circulated between the second recharger and the second module.

21. The method of claim 1, wherein fluid is directed from the recharger into the reusable module, and then into a bypass line, bypassing the second module.

22. The method of claim 1, wherein the reusable module contains zirconium phosphate, and wherein the recharger contains a solution having sodium and hydrogen ions.

* * * * *